United States Patent
Sanchez et al.

(10) Patent No.: US 9,453,035 B2
(45) Date of Patent: Sep. 27, 2016

(54) HALOGEN FREE SYNTHESES OF AMINOSILANES BY CATALYTIC DEHYDROGENATIVE COUPLING

(71) Applicant: Voltaix, LLC, Branchburg, NJ (US)

(72) Inventors: Antonio Sanchez, Jersey City, NJ (US); Gennadiy Itov, Flemington, NJ (US); Peng Zhang, Montvale, NJ (US); Matthew Damien Stephens, Morristown, NJ (US)

(73) Assignee: VOLTAIX, LLC, Branchburg, NJ (US)

( * ) Notice: Subject to any disclaimer, the term of this patent is extended or adjusted under 35 U.S.C. 154(b) by 0 days.

(21) Appl. No.: 15/088,495

(22) Filed: Apr. 1, 2016

(65) Prior Publication Data

US 2016/0215003 A1    Jul. 28, 2016

Related U.S. Application Data

(62) Division of application No. 14/491,581, filed on Sep. 19, 2014.

(60) Provisional application No. 61/883,452, filed on Sep. 27, 2013.

(51) Int. Cl.
*C07F 7/04*    (2006.01)
*C07F 7/02*    (2006.01)

(52) U.S. Cl.
CPC .................................... *C07F 7/025* (2013.01)

(58) Field of Classification Search
CPC ... C07C 45/68; C07C 253/30; C07C 213/02; C07C 213/08; C07C 251/12
USPC .......................................................... 556/413
See application file for complete search history.

(56) References Cited

PUBLICATIONS

Schuh et al., Z. Anorg. Allg. Chem. (1993), 619(8), 1347-1352.*

* cited by examiner

*Primary Examiner* — Porfirio Nazario Gonzalez
*Assistant Examiner* — Kofi Adzamli

(57) ABSTRACT

Compounds and method of preparation of Si—X and Ge—X compounds (X=N, P, As and Sb) via dehydrogenative coupling between the corresponding unsubstituted silanes and amines (including ammonia) or phosphines catalyzed by metallic catalysts is described. This new approach is based on the catalytic dehydrogenative coupling of a Si—H and a X—H moiety to form a Si—X containing compound and hydrogen gas (X=N, P, As and Sb). The process can be catalyzed by transition metal heterogenous catalysts such as Ru(0) on carbon, Pd(0) on MgO) as well as transition metal organometallic complexes that act as homogeneous catalysts. The —Si—X products produced by dehydrogenative coupling are inherently halogen free. Said compounds can be useful for the deposition of thin films by chemical vapor deposition or atomic layer deposition of Si-containing films.

4 Claims, 2 Drawing Sheets

HALOGEN FREE SYNTHESES OF AMINOSILANES BY CATALYTIC DEHYDROGENATIVE COUPLING

CROSS-REFERENCE TO RELATED APPLICATIONS

This Application is a divisional application of application Ser. No. 14/491,581, filed on Sep. 19, 2014, which claims priority from U.S. Provisional Patent Application No. 61/883,452 filed on Sep. 27, 2013. The priority of each prior mentioned application is claimed. Each of prior mentioned applications is hereby incorporated by reference herein in its entirety.

BACKGROUND OF THE INVENTION

Most of processes found in the literature to form silicon-heteroatom and germanium heteroatom bonds involve the reaction of a chlorosilane and a nucleophile (amine, phosphine, etc). These reactions are based on a net dehydrohalogenation thus forming one equivalent of a hydrogen halide which needs to be scavenged by a base, forming large amounts of salt which need to be filtered out. This fact also limits the scope of the reaction to base-compatible substrates and results in products contaminated with a halogens such as chlorine and aminohalogens.

Silane compounds such as monosilane, disilane and trisilane are used in a variety of applications. In the field of semiconductors, silane compounds are frequently used as starting materials (precursors) for the production by chemical vapor deposition (CVD) of silicon-based dielectric films of, e.g., silicon nitride, silicon oxide, or silicon oxynitride. More specifically, silane compounds can produce silicon nitride by reaction with a nitrogen-containing reaction gas such as ammonia, silicon oxide by reaction with an oxygen-containing gas such as oxygen, and silicon oxynitride by reaction with a nitrogen-containing gas and an oxygen-containing gas.

At present the standard method for producing silicon nitride films by CVD involves inducing a reaction between ammonia gas or other amine (the amino compound) and a halosilane such as chlorosilane (the silane compound); however, ammonium chloride or amine hydrochloride is produced as a by-product by this reaction. Ammonium chloride is a white solid and as such accumulates in and clogs the exhaust lines of the CVD reaction apparatus. Amine hydrochloride salts are highly undesirable contaminants in aminosilanes used for electrical applications because they can react with metals in the CVD chamber and degrade the electrical properties of the semiconductor material or lead the creation of other types of defects. More than that, these salts are known to sublimate by a dissociation-recombination process generating HCl. Hydrogen chloride is a corrosive gas that can damage any process taking place in the CVD chamber as well as the chamber itself. Reactive chlorine from these or any other sources may cause these deleterious effects. Silane compounds synthesized without using halogen containing reactants thereby being free of halogens and aminohalogens are highly desirable.

In CVD methods, it is therefore desired to have a precursor compound that is halogen free.

DETAILED DESCRIPTION OF THE INVENTION

Figure 1:
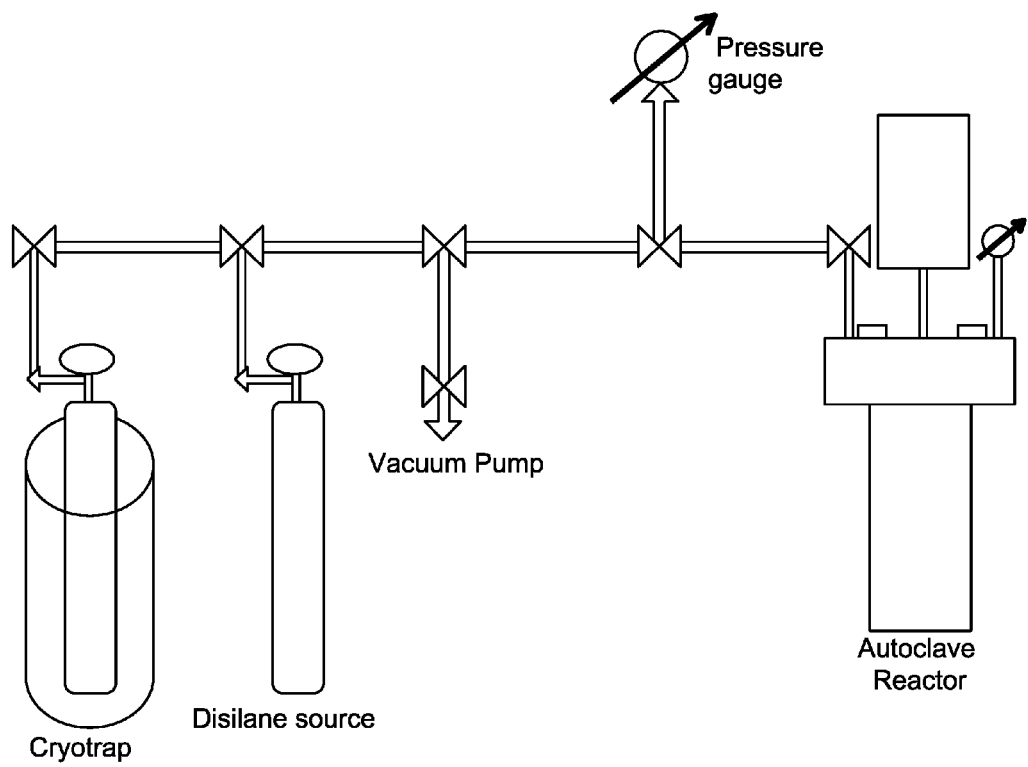
FIG. 1 is a typical reactor apparatus wherein the reaction vessel is an autoclave reactor fitted with a stirrer and connected to a manifold capable of providing vacuum and reactants.
Figure 2:
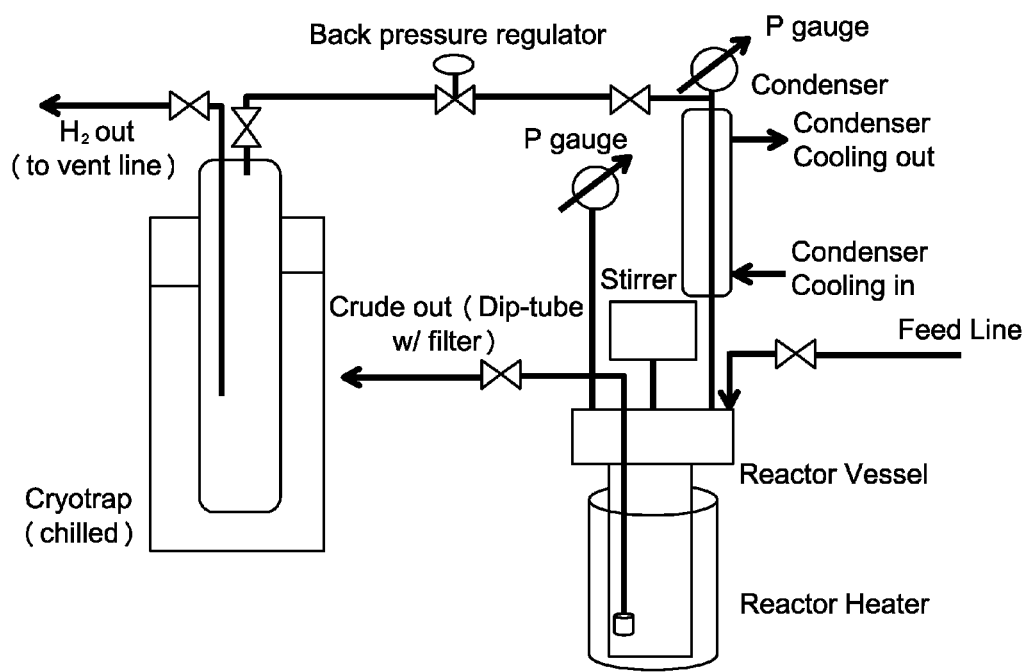
FIG. 2 is a typical reactor apparatus wherein the reactor vessel is attached to a condenser allowing for hydrogen venting and a Dip-tube with filter for removal of the product.

A method for the synthesis of compounds having silicon-heteroatom (X) bonds or germanium heteroatom bonds without the formation of halogen byproducts has been developed. The starting materials for the dehydrogenative coupling synthesis methods described herein are not halogen containing compounds. All of the compounds produced by the dehydrogenative coupling synthesis described and claimed herein are "halogen free" without further purification, as the term "halogen free" is defined herein. It is believed that when halogens are present in precursor compounds, these compounds are less stable. The compounds of the present invention are claimed in two forms. First, as new compounds and second as compounds that are prepared halogen free without further purification to remove halogens. Silicon and germanium are group IVb elements. This approach is based on the catalytic dehydrocoupling of silicon or germanium with a heteroatom, releasing hydrogen gas. A Si—X or Ge—X bond is formed where X is a group Vb element selected from the group consisting of Nitrogen (N), Phosphorus (P), Arsenic (As) and Antimony (Sb). The process is catalyzed by transition metal catalysts. Catalysts may be heterogeneous or homogeneous. An illustration of the general reaction for an amine is given by equation 1. An illustration of the general reaction for the group Vb heteroatoms N, P, As or Sb and the group IVb elements is given in equation 1A. The reaction may be carried out in a solvent or without a solvent. The reaction may be carried out in a batch or continuous flow reactor.

$$R^1EH_{3+n}(R^2R^3NH) = (R^2R^3N)_n EH_{(3-n)}R^1 + nH_2 \quad\quad 1.$$

$$R^1EH^3+n(R^2R^3XH) = (R^2R^3X)_n EH_{(3-n)}R^1 + nH_2 \quad\quad 1A.$$

Where X=N, P, As or Sb; n=1, 2 or 3; E is a group IVb element selected from the group consisting of Si or Ge; X is a hetero atom selected from the group consisting of N, P, As or Sb; $R^1$=H, $H_3E$-, $H_5E_2$-; $H_7E_3$-; $H_9E_4$-; $H_{11}E_5$-; and $R^2$=H, linear or branched $C_1$ to $C_6$ alkyl, linear or branched $C_1$ to $C_8$ alkenyl, linear or branched $C_1$ to $C_8$ alkynyl, $C_6$ to $C_{10}$ aryl, linear or branched $C_1$ to $C_6$ alkyl ether, silyl, trimethyl silyl, or linear or branched $C_1$ to $C_6$ alkyl-substituted silyl, and $R_3$ is H, linear or branched $C_1$ to $C_6$ alkyl, linear or branched $C_1$ to $C_8$ alkenyl, linear or branched $C_1$ to $C_8$ alkynyl, $C_6$ to $C_{10}$ aryl, linear or branched $C_1$ to $C_6$ alkyl ether, silyl, trimethyl silyl, or linear or branched $C_1$ to $C_6$ alkyl-substituted silyl. In equation 1 above, the amine $R^2R^3NH$ may be replaced by a diamine, a triamine, a tetra amine, a silazane and a cyclic secondary amine. Non-limiting examples of a diamine include ethylene diamine, 1,2-propylene diamine and similar diamines. Non-limiting examples of a triamine include diethylene triamine and similar compounds. Non-limiting examples of a tetra amine include triethylenetetraamine and similar compounds. Non-limiting examples of a silazane include hexamethyl disilazane. Non-limiting examples of a cyclic secondary amines include aziridine, azetidine, piperidine, pyrrolidine, pyrrole, imidazole, pyrazole, indole or any C-substituted derivatives of the cyclic secondary amine and similar compounds. A non-limiting list of C-substituted derivatives of the cyclic secondary amines includes any alkyl substituted derivatives of cyclic secondary amines such as 2-methyl piperidine, 3-methyl piperidine, 4-methyl piperidine, 2-methyl pyrrolidine, 3-methyl pyrrolidine, 2-methyl pyrrole, 3-methyl pyrrole, 2-methyl indole, and 3-methyl indole. Secondary cyclic amines are heterocycles containing one or more N groups and several carbon atoms in the backbone chain (ring). For example piperidine contains 5 carbons and 1 nitrogen in hexagonal ring structure. Each carbon is attached to two pendant hydrogens, and the nitrogen is attached to one pendant hydrogen. A carbon-substituted heterocyclic secondary amine contains a heterocyclic ring structure with pendant substituent groups other than hydrogen attached to one or more carbon atoms that make up the ring. Typical pendant substituent groups include: but are not limited to alkyl, alkenyl, alkynyl, aryl, alkyl ether, silyl, trimethyl silyl, or alkyl-substituted silyl. In equation 1A, when X is P, As or Sb, $R^1$=$H_3$E-, $H_5E_2$-; $H_7E_3$-; $H_9E_4$-; $H_{11}E_5$-; $R^2$=H, linear or branched $C_1$ to $C_6$ alkyl, linear or branched $C_1$ to $C_8$ alkenyl, linear or branched $C_1$ to $C_8$ alkynyl, $C_6$ to $C_{10}$ aryl, linear or branched $C_1$ to $C_6$ alkyl ether, silyl, trimethyl silyl, or linear or branched $C_1$ to $C_6$ alkyl-substituted silyl, and $R_3$ is H, linear or branched $C_1$ to $C_6$ alkyl, linear or branched $C_1$ to $C_8$ alkenyl, linear or branched $C_1$ to $C_8$ alkynyl, $C_6$ to $C_{10}$ aryl, linear or branched $C_1$ to $C_6$ alkyl ether, trimethyl silyl, or linear or branched $C_1$ to $C_6$ alkyl-substituted silyl. The said compounds exclude compounds where $R^1$ is $H_3$E and $R^2$ and $R^3$ are independently $C_1$ or $C_2$ alkyl.

A non-limiting list of the members of the alkyl substituent groups comprises: methyl, ethyl, propyl, iso-propyl, butyl, tert-butyl, sec-butyl, iso-butyl, pentyl, neopentyl, isopentyl, hexyl, isohexyl. A non-limiting list of the members of the aryl substituent groups comprises: phenyl, tolyl, xylyl, napthyl, pyridyl.

alkenyl is defined as any univalent aliphatic hydrocarbon radical $C_nH_{2n-1}$ (such as 2-butenyl $CH_3CH{:}CHCH_2$—) derived from an alkene by removal of one hydrogen atom. Where n=2 to 8.

Alkynyl is defined as Any of a series of open chain hydrocarbons with a carbon-carbon triple bond and the general formula $C_nH_{2n-2}$. Where n=2 to 8.

Depending on the structure of the heteroatom compound and structure of the Si or Ge compound and the molar ratio of E to X a number of molecules containing E-X bonds can be formed. These molecules containing E-X bonds may be linear, branched, cyclic or combinations thereof. Examples linear, branched and cyclic and combinations and a method of synthesizing each are described.

A method for preparing the compound having the formula:

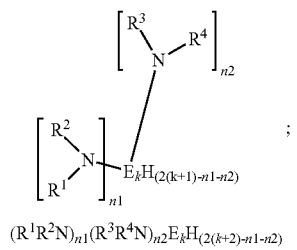

$(R^1R^2N)_{n1}(R^3R^4N)_{n2}E_kH_{2(k+2)-n1-n2}$ where $n_1$=1 to $(2(k+1)-n_2)$; $n_2$=0 to $(2(k+1)-n_1)$; k=2 to 6; $R^1$, $R^2$, $R^3$ and $R^4$ are independently selected from the group consisting of linear or branched $C_1$ to $C_6$ alkyl, linear or branched $C_1$ to $C_8$ alkenyl, linear or branched $C_1$ to $C_8$ alkynyl, $C_6$ to $C_{10}$ aryl, linear or branched $C_1$ to $C_6$ alkyl ether, silyl, trimethyl silyl, or linear or branched $C_1$ to $C_6$ alkyl-substituted silyl; E is a group IVb element selected from the group consisting of Si or Ge. The following compounds that are not halogen free can be made by methods that include a halogen containing reactant and are excluded from the composition of matter claims contained herein but are not excluded from the method of synthesis claims contained herein. The excluded compounds include: $[(R^1R^2N)_{3-x}H_xSi{-}Si(NR^3R^4)_{3-y}H_y]$ wherein $R^1$, $R^2$, $R^3$ and $R^4$ are independently any substituted or unsubstituted linear, branched or cyclic alkyl group, and x,y=0, 1 or 2, $(R^1R^2N)_n{-}SiH_{(3-n)}SiH_3$, wherein $R^1$ is selected from a linear or branched $C_3$ to $C_{10}$ alkyl group, a linear or branched $C_3$ to $C_{10}$ alkenyl group, a linear or branched $C_3$ to $C_{10}$ alkynyl group, a $C_1$ to $C_6$ dialkylamino group, an electron withdrawing group, a $C_3$ to $C_{10}$ cyclic alkyl group, and a $C_6$ to $C_{10}$ aryl group; $R^2$ is selected from H, linear or branched $C_1$ to $C_{10}$ alkyl group, a linear or branched $C_3$ to $C_6$ alkenyl group, a linear or branched $C_3$ to $C_6$ alkynyl group, a $C_1$ to $C_6$ dialkylamino group, a $C_3$ to $C_{10}$ cyclic alkyl group, a $C_6$ to $C_{10}$ aryl group, an electron withdrawing group and a $C_4$ to $C_{10}$ aryl group; n=1 or 2; wherein $R^1$ and $R^2$ are linked together to form a ring selected from a substituted or unsubstituted aromatic ring or a substituted or unsubstituted aliphatic ring; and when n=2, and $R^1$ and or $R^2$ or both $R^1$, or both $R^2$ are linked together to form a ring, $((R)HN)_3{-}Si{-}Si{-}(NH(R))_3$. Each R is independently selected from $C_1$ to $C_4$ hydrocarbyl, $(Et_2N)SiH_2{-}SiH_2(NEt_2)$, $(Et_2N)SiH_2{-}SiH_2{-}SiH_2(NEt_2)$, $SiH_3{-}SiH(NEt_2){-}SiH(NEt_2){-}SiH_3$, $[(CH_3)_3Si{-})_2N]{-}SiH_2{-}SiH_2{-}SiH_2{-}[N({-}Si(CH_3)_3)_2]$, $[(CH_3)_3Si{-})_2N]{-}SiH_2{-}SiH_2{-}SiH_2{-}SiH_2{-}[N({-}Si(CH_3)_3)_2]$,

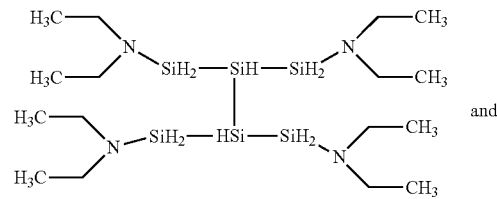

and

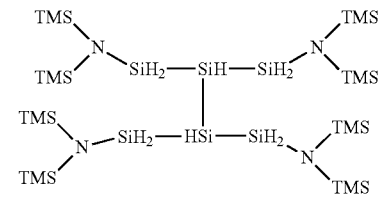

(TMS=trimethylsilane) and further excluding $H_3SiNEt_2$ which has been reported as being halogen free.

a) contacting the reactants $R^1R^2NH$ and $R^3R^4NH$ and $E_kH_{2(k+1)}$ in the presence of a transition metal catalyst forming a reaction mixture;
b) optionally adding a solvent to the reaction mixture;
c) maintaining the reaction mixture at a temperature between about 0° C. to about 300° C.;
d) allowing the reaction to proceed to form $(R^1R^2N)_{n1}(R^3R^4N)_{n2}E_kH_{2(k+1)-n1-n2}$;
e) separating the $(R^1R^2N)_{n1}(R^3R^4N)_{n2}E_kH_{2(k+1)-n1-n2}$ from the reaction mixture;
wherein the reaction mixture temperature may vary during the synthesis and is maintained such that the temperature of the reaction mixture is not allowed to drop below about 0° C. and not exceed about 300° C.

Structure formula for k=3; $R^1=R^2$=isopropyl; $n_1=1$; $n_2=0$.

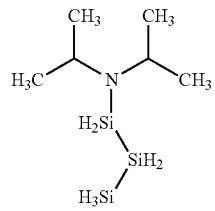

A method for preparing the compound having the formula:

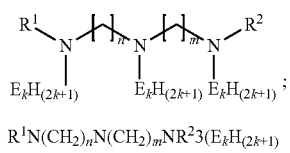

$R^1N(CH_2)_nN(CH_2)_mNR^23(E_kH_{(2k+1)})$ where n=1 to 6; m=1 to 6; k=1 to 6; $R^1$ and $R^2$ are independently selected from the group consisting of linear or branched $C_1$ to $C_6$ alkyl, linear or branched $C_1$ to $C_8$ alkenyl, linear or branched $C_1$ to $C_8$ alkynyl, $C_6$ to $C_{10}$ aryl, linear or branched $C_1$ to $C_6$ alkyl ether, silyl, trimethyl silyl, or linear or branched $C_1$ to $C_6$ alkyl-substituted silyl; E is a group IVb element selected from the group consisting of Si or Ge:

a) contacting the reactants $R^1NH(CH_2)_nNH(CH_2)_mNHR^2$ and $E_kH_{(2k+2)}$, in the presence of a transition metal catalyst forming a reaction mixture; where the molar ratio of $HE_kH_{(2k+1)}$ to $R^1NH(CH_2)_nNH(CH_2)_mNHR^2$ is at least 3:1;

b) optionally adding a solvent to the reaction mixture;

c) maintaining the reaction mixture at a temperature between about 0° C. to about 300° C.;

d) allowing the reaction to proceed to form $R^1N(CH_2)_nN(CH_2)_mNR^23(E_kH_{(2k+1)})$;

e) separating the product $R^1N(CH_2)_nN(CH_2)_mNR^23(E_kH_{(2k+1)})$ from the reaction mixture; wherein the reaction temperature may vary during the synthesis and is maintained such that the temperature of the reaction mixture is not allowed to drop below about 0° C. and not exceed about 300° C.

Structure for k=3; $R^1$=ethyl; $R^2$=ethyl; n=1; m=1:

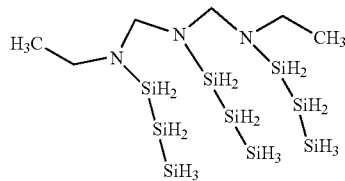

A method for preparing the compound having the formula:

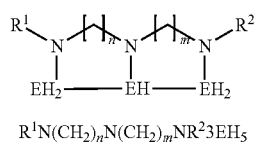

$R^1N(CH_2)_nN(CH_2)_mNR^23EH_5$ where one E is attached to 3 Nitrogens; n=1 to 6; m=1 to 6; $R^1$ and $R^2$ are independently selected from the group consisting of linear or branched $C_1$ to $C_6$ alkyl, linear or branched $C_1$ to $C_8$ alkenyl, linear or branched $C_1$ to $C_8$ alkynyl, $C_6$ to $C_{10}$ aryl, linear or branched $C_1$ to $C_6$ alkyl ether, silyl, trimethyl silyl, or linear or branched $C_1$ to $C_6$ alkyl-substituted silyl; E is a group IVb element selected from the group consisting of Si or Ge:

a) contacting the reactants $R^1NH(CH_2)_nNH(CH_2)_mNHR^2$ and $HE_3H_5$ in the presence of a transition metal catalyst forming a reaction mixture;

b) optionally adding a solvent to the reaction mixture;

c) maintaining the reaction mixture at a temperature between about 0° C. to about 300° C.;

d) allowing the reaction to proceed to form $R^1N(CH_2)_nN(CH_2)_mNR^23EH_5$;

e) separating the product $R^1N(CH_2)_nN(CH_2)_mNR^23EH_5$ from the reaction mixture;

wherein the reaction mixture temperature may vary during the synthesis and is maintained such that the temperature of the reaction mixture is not allowed to drop below about 0° C. and not exceed about 300° C.

Sample structure for k=3; $R^1$=ethyl; $R^2$=ethyl; n=1; m=1:

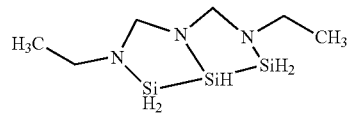

A method for preparing the compound having the formula:

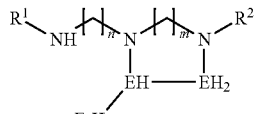

$R^1N(CH_2)_nN(CH_2)_mNR^2E_2H_3E_kH_{(2k+1)}$ where n=1 to 6; m=1 to 6; k=1 to 6; $R^1$ and $R^2$ are independently selected from the group consisting of linear or branched $C_1$ to $C_6$ alkyl, linear or branched $C_1$ to $C_8$ alkenyl, linear or branched $C_1$ to $C_8$ alkynyl, $C_6$ to $C_{10}$ aryl, linear or branched $C_1$ to $C_6$ alkyl ether, silyl, trimethyl silyl, or linear or branched $C_1$ to $C_6$ alkyl-substituted silyl; E is a group IVb element selected from the group consisting of Si or Ge:

a) contacting the reactants $R^1NH(CH_2)_nNH(CH_2)_mNHR^2$ and $HE_2H_4E_kH_{(2k+1)}$ in the presence of a transition metal catalyst forming a reaction mixture;

b) optionally adding a solvent to the reaction mixture;

c) maintaining the reaction mixture at a temperature between about 0° C. to about 300° C.;

d) allowing the reaction to proceed to form $R^1N(CH_2)_nN(CH_2)_mNR^2E_2H_3(E_kH_{2k+1})$;

e) separating the $R^1N(CH_2)_nN(CH_2)_mNR^2E_2H_3(E_kH_{2k+1})$ from the reaction mixture;

wherein the reaction temperature may vary during the synthesis and is maintained such that the temperature of the reaction mixture is not allowed to drop below about 0° C. and not exceed about 300° C.

Sample structure for k=3; $R^1$=ethyl; $R^2$=ethyl; n=1; m=1:

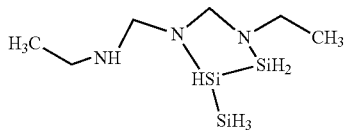

A method for preparing the compound having the formula:

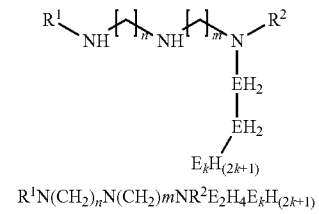

$R^1N(CH_2)_nN(CH_2)_mNR^2E_2H_4E_kH_{(2k+1)}$ where one E is attached to one nitrogen; n=1 to 6; m=1 to 6; k=1 to 6; $R^1$ and $R^2$ are independently selected from the group consisting of linear or branched $C_1$ to $C_6$ alkyl, linear or branched $C_1$ to $C_8$ alkenyl, linear or branched $C_1$ to $C_8$ alkynyl, $C_6$ to $C_{10}$ aryl, linear or branched $C_1$ to $C_6$ alkyl ether, silyl, trimethyl silyl, or linear or branched $C_1$ to $C_6$ alkyl-substituted silyl; E is a group IVb element selected from the group consisting of Si or Ge:
a) contacting the reactants $R^1NH(CH_2)_nNH(CH_2)_mNHR^2$ and $HE_2H_4E_kH_{(2k+1)}$ in the presence of a transition metal catalyst forming a reaction mixture;
b) optionally adding a solvent to the reaction mixture;
c) maintaining the reaction mixture at a temperature between about 0° C. to about 300° C.;
d) allowing the reaction to proceed to form $R^1N(CH_2)_nN(CH_2)_mNR^2E_2H_4E_kH_{(2k+1)}$;
e) separating the $R^1N(CH_2)_nN(CH_2)_mNR^2E_2H_4E_kH_{(2k+1)}$ from the reaction mixture;
wherein the reaction temperature may vary during the synthesis and is maintained such that the temperature of the reaction mixture is not allowed to drop below about 0° C. and not exceed about 300° C.

Structure for k=1; $R^1$=ethyl; $R^2$=ethyl; n=1; m=1:

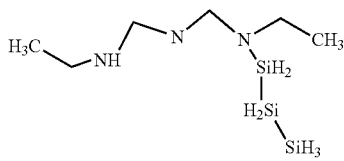

A method for preparing the compound having the formula:

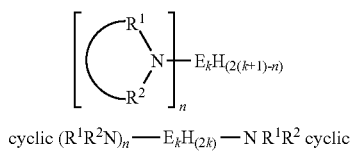

cyclic $(R^1R^2N)_n$—$E_kH_{(2k)}$—N $R^1R^2$ cyclic

Compositions having a cyclic secondary amine structure above are referred to as "cyclic $R^1R^2N$—".

Where: n=1 or 2; k=2 to 6; $R^1$ and $R^2$ are independently selected from the group consisting of —CHR'—; —CHR'—CHR"—; —CHR'—CHR"—CHR'"—; =CH—; —CR'=CR"—; —CR'=N—CR"—; =CH—; —CHR'=CHR"— and R', R", and R'" are independently selected from the group consisting of linear or branched $C_1$ to $C_6$ alkyl, linear or branched $C_1$ to $C_8$ alkenyl, linear or branched $C_1$ to $C_8$ alkynyl, $C_6$ to $C_{10}$ aryl, linear or branched $C_1$ to $C_6$ alkyl ether, silyl, trimethyl silyl, or linear or branched $C_1$ to $C_6$ alkyl-substituted silyl; and E is a group IVb element selected from the group consisting of Si or Ge. The following compounds that are not halogen free can be made by methods that include a halogen containing reactant and are excluded from the composition of matter claims contained herein but are not excluded from the method of synthesis claims contained herein. The excluded compounds include:

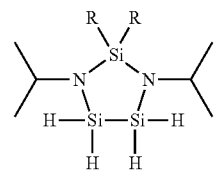

and wherein R=$CH_3$, Ph.
a) contacting the reactants cyclic $R^1R^2NH$ and $HE_kH_{(2k+1)}$, in the presence of a transition metal catalyst forming a reaction mixture; where the molar ratio of $HE_kH_{(2k+1)}$ to cyclic $R^1R^2NH$ is at least 3:1;
b) optionally adding a solvent to the reaction mixture;
c) maintaining the reaction mixture at a temperature between about 0° C. to about 300° C.;
d) allowing the reaction to proceed to form cyclic $R^1R^2N$-$E_kH_{(2k+1)}$);
e) separating the cyclic $R^1R^2N$-$E_kH_{(2k+1)}$) from the reaction mixture;
wherein the reaction mixture temperature may vary during the synthesis and is maintained such that the temperature of the reaction mixture is not allowed to drop below about 0° C. and not exceed about 300° C.

Structure for k=3; cyclic $R^1R^2NH$=pyrrolidine; $R^1$ and $R^2$=—CHR'—CHR"—; and R', R"=H:

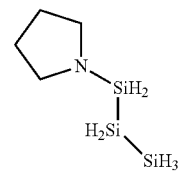

A method for the synthesis of a compound having the formula:

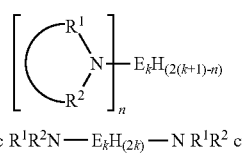

cyclic $R^1R^2N$—$E_kH_{(2k)}$—N $R^1R^2$ cyclic

Wherein: n=1 or 2; k=1 to 6; $R^1$ and $R^2$ are independently selected from the group consisting of —CHR'—; —CHR'—

CHR"—; —CHR'—CHR"—CHR'''—; =CH—; —CR'=CR"—; —CR'=N—CR"=; =CH—; —CHR'=CHR"— and R', R", and R''' are independently selected from the group consisting of linear or branched $C_1$ to $C_6$ alkyl, linear or branched $C_1$ to $C_8$ alkenyl, linear or branched $C_1$ to $C_8$ alkynyl, $C_6$ to $C_{10}$ aryl, linear or branched $C_1$ to $C_6$ alkyl ether, silyl, trimethyl silyl, or linear or branched $C_1$ to $C_6$ alkyl-substituted silyl; and E is a group IVb element selected from the group consisting of Si or Ge. The said compounds exclude the following halogen free compounds wherein n=2; k=1, E=Si and $R^1,R^2$ are both —CR'=CR"— and wherein R' and R" are both H.

a) contacting the reactants cyclic $R^1R^2NH$ and $HE_kH_{(2k+1)}$, in the presence of a transition metal catalyst forming a reaction mixture; where the molar ratio of $HE_kH_{(2k+1)}$ to cyclic $R_1R^2NH$ is about 1:1 to about 1:5;

b) optionally adding a solvent to the reaction mixture;

c) maintaining the reaction mixture at a temperature between about 0° C. to about 300° C.;

d) allowing the reaction to proceed to form cyclic $R^1R^2N$-$E_kH_{(2k)}$—$NR^1R^2$ cyclic;

e) separating the cyclic $R^1R^2N$-$E_kH_{(2k)}$—$NR^1R^2$ cyclic from the reaction mixture;

wherein the reaction temperature may vary during the synthesis and is maintained such that the temperature during the reaction is not allowed to drop below about 0° C. and not exceed about 300° C.

Preferably, the secondary cyclic amine is selected from the group consisting of aziridine, azetidine, piperidine, pyrrolidine, pyrrole, imidazole, pyrazole, indole or any C-substituted derivatives of the cyclic secondary amine; E is a group IVb element selected from the group consisting of Si or Ge.

The terms chlorine free, halide free, halogen free and aminochlorine free and aminohalogen free are used herein to define compounds that contain less than 5 ppm of halogen, preferably less than 3 ppm halogen and more preferably less than 1 ppm halogen. The term halogen includes fluorine, chlorine, bromine and iodine. In order to achieve halogen free products, the starting reactants and catalyst of the present invention are halogen free. The terms aminohalide and aminohalogen refer to any amine including but not limited to ammonia, and organic amines which are associated with a halogen. This association may be a salt, a complex or a chemical bond. The terms "reaction vessel" and "reactor" refer to the same equipment, have the same meaning and are used interchangeably herein. The reactor may be a vessel for batch synthesis or a flow through vessel to facilitate a continuous synthesis. The term "reaction mixture" refers to the combination of reactants, catalyst and optionally solvent wherein a reaction takes place to form the product. The term "halogen free" as used in this disclosure and the claims refers to the level of halogen present from all sources such as but not limited to halogen ions, bound halogen and aminohalogens.

A compound having the formula:

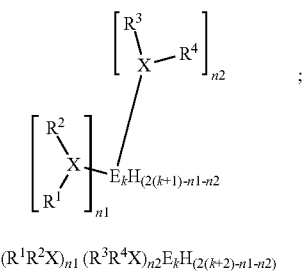

$(R^1R^2X)_{n1} (R^3R^4X)_{n2}E_kH_{(2k+2)-n1-n2}$ where X=P, As, Sb; where $n_1=1$; $n_2=0$ to $(2(k+2)-n_1)$; $k=1$ to 6; $R^1$, $R^2$, $R^3$ and $R^4$ are independently selected from the group consisting of linear or branched $C_1$ to $C_6$ alkyl, linear or branched $C_1$ to $C_8$ alkenyl, linear or branched $C_1$ to $C_8$ alkynyl, $C_6$ to $C_{10}$ aryl, linear or branched $C_1$ to $C_6$ alkyl ether, silyl, trimethyl silyl, or linear or branched $C_1$ to $C_6$ alkyl-substituted silyl; E is a group IVb element selected from the group consisting of Si or Ge.

A method of preparing the compounds having the structure $(R^1R^2X)_{n1} (R^3R^4X)_{n2}E_kH_{(2k+2)-n1-n2}$, comprising:

a) contacting the reactants $R^1R^2XH$ and $R^3R^4XH$ and $E_kH_{2(k+1)}$ in the presence of a transition metal catalyst forming a reaction mixture;

b) optionally adding a solvent to the reaction mixture;

c) maintaining the reaction mixture at a temperature between about 0° C. to about 300° C.;

d) allowing the reaction to proceed to form $(R^1R^2X)_{n1}$ $(R^3R^4X)_{n2}E_kH_{(2(k+1)-n1-n2)}$;

e) separating the $(R^1R^2X)_{n1} (R^3R^4X)_{n2}E_kH_{(2(k+1)-n1-n2)}$ from the reaction mixture;

wherein the reaction mixture temperature may vary during the synthesis and is maintained such that the temperature of the reaction mixture is not allowed to drop below about 0° C. and not exceed about 300° C.

A compound having the formula:

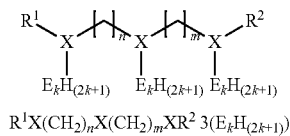

$R^1X(CH_2)_nX(CH_2)_mXR^2\ 3(E_kH_{(2k+1)})$ where X=P, As, Sb; where n=1 to 6; m=1 to 6; k=1 to 6; $R^1$=H, linear or branched $C_1$ to $C_6$ alkyl, linear or branched $C_1$ to $C_8$ alkenyl, linear or branched $C_1$ to $C_8$ alkynyl, $C_6$ to $C_{10}$ aryl, linear or branched $C_1$ to $C_6$ alkyl ether, silyl, trimethyl silyl, or linear or branched $C_1$ to $C_6$ alkyl-substituted silyl; $R^2$=H, linear or branched $C_1$ to $C_6$ alkyl, linear or branched $C_1$ to $C_8$ alkenyl, linear or branched $C_1$ to $C_8$ alkynyl, $C_6$ to $C_{10}$ aryl, linear or branched $C_1$ to $C_6$ alkyl ether, silyl, trimethyl silyl, or linear or branched $C_1$ to $C_6$ alkyl-substituted silyl; E is a group IVb element selected from the group consisting of Si or Ge.

A method of preparing the compounds having the structure $R^1X(CH_2)_nX(CH_2)_mXR^23(E_kH_{(2k+1)})$, comprising:

a) contacting the reactants $R^1XH(CH_2)_nXH(CH_2)_mXHR^2$ and $HE_kH_{(2k+1)}$, in the presence of a transition metal catalyst forming a reaction mixture; where the molar ratio of $HE_kH_{(2k+1)}$ to $R^1XH(CH_2)_nXH(CH_2)_mXHR^2$ is at least 3:1;

b) optionally adding a solvent to the reaction mixture;

c) maintaining the reaction mixture at a temperature between about 0° C. to about 300° C.;

d) allowing the reaction to proceed to form $R^1X(CH_2)_nX(CH_2)_mXR^23(E_kH_{(2k+1)})$;

e) separating the product $R^1X(CH_2)_nX(CH_2)_mXR^2$ $3(E_kH_{(2k+1)})$ from the reaction mixture;

wherein the reaction temperature may vary during the synthesis and is maintained such that the temperature of the reaction mixture is not allowed to drop below about 0° C. and not exceed about 300° C.

A compound having the formula:

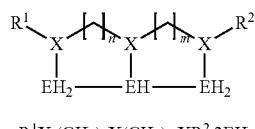

$R^1X(CH_2)_nX(CH_2)_mXR^2 \cdot 3EH_5$ where X=P, As, Sb; n=1 to 6; m=1 to 6; k=3 to 6; $R^1$=H, linear or branched $C_1$ to $C_6$ alkyl, linear or branched $C_1$ to $C_8$ alkenyl, linear or branched $C_1$ to $C_8$ alkynyl, $C_6$ to $C_{10}$ aryl, linear or branched $C_1$ to $C_6$ alkyl ether, silyl, trimethyl silyl, or linear or branched $C_1$ to $C_6$ alkyl-substituted silyl; $R^2$=H, linear or branched $C_1$ to $C_6$ alkyl, linear or branched $C_1$ to $C_8$ alkenyl, linear or branched $C_1$ to $C_8$ alkynyl, $C_6$ to $C_{10}$ aryl, linear or branched $C_1$ to $C_6$ alkyl ether, silyl, trimethyl silyl, or linear or branched $C_1$ to $C_6$ alkyl-substituted silyl; E is a group IVb element selected from the group consisting of Si or Ge.

A method of preparing the compounds having the structure $R^1X(CH_2)_nX(CH_2)_mXR^2 \cdot 3EH_5$, comprising:
a) contacting the reactants $R^1XH(CH_2)_nXH(CH_2)_mXHR^2$ and $HE_3H_5$ in the presence of a transition metal catalyst forming a reaction mixture;
b) optionally adding a solvent to the reaction mixture;
c) maintaining the reaction mixture at a temperature between about 0° C. to about 300° C.;
d) allowing the reaction to proceed to form $R^1X(CH_2)_nX(CH_2)_mXR^2 \cdot 3EH_5$;
e) separating the product $R^1X(CH_2)_nX(CH_2)_mXR^2 \cdot 3EH_5$ from the reaction mixture;
wherein the reaction mixture temperature may vary during the synthesis and is maintained such that the temperature of the reaction mixture is not allowed to drop below about 0° C. and not exceed about 300° C.

A compound having the formula:

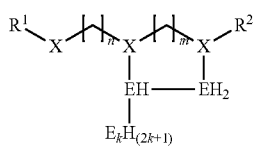

$R^1X(CH_2)_nX(CH_2)_mX R^2 \cdot E_2H_3E_kH_{(2k+1)}$ where X=P, As, Sb; n=1 to 6; m=1 to 6; k=2 to 6; $R^1$=H, linear or branched $C_1$ to $C_6$ alkyl, linear or branched $C_1$ to $C_8$ alkenyl, linear or branched $C_1$ to $C_8$ alkynyl, $C_6$ to $C_{10}$ aryl, linear or branched $C_1$ to $C_6$ alkyl ether, silyl, trimethyl silyl, or linear or branched $C_1$ to $C_6$ alkyl-substituted silyl; $R^2$=H, linear or branched $C_1$ to $C_6$ alkyl, linear or branched $C_1$ to $C_8$ alkenyl, linear or branched $C_1$ to $C_8$ alkynyl, $C_6$ to $C_{10}$ aryl, linear or branched $C_1$ to $C_6$ alkyl ether, silyl, trimethyl silyl, or linear or branched $C_1$ to $C_6$ alkyl-substituted silyl; E is a group IVb element selected from the group consisting of Si or Ge.

A method of preparing the compounds having the structure $R^1X(CH_2)_nX(CH_2)_mXR^2E_2H_3E_kH_{(2k+1)}$, comprising:
a) contacting the reactants $R^1XH(CH_2)_nXH(CH_2)_mXHR^2$ and $HE_2H_3E_kH_{2k}$ in the presence of a transition metal catalyst forming a reaction mixture;
b) optionally adding a solvent to the reaction mixture;
c) maintaining the reaction mixture at a temperature between about 0° C. to about 300° C.;
d) allowing the reaction to proceed to form $R^1X(CH_2)_nX(CH_2)_mXR^2E_2H_3E_kH_{(2k+1)}$;
e) separating the $R^1X(CH_2)_nX(CH_2)_mXR^2E_2H_3E_kH_{(2k+1)}$ from the reaction mixture;
wherein the reaction temperature may vary during the synthesis and is maintained such that the temperature of the reaction mixture is not allowed to drop below about 0° C. and not exceed about 300° C.

A compound having the formula:

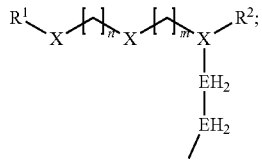

$R^1X(CH_2)_nX(CH_2)_mX R^2E_kH_{(2k+1)}$ where X=P, As, Sb; n=1 to 6; m=1 to 6; k=1 to 6; $R^1$=H, linear or branched $C_1$ to $C_6$ alkyl, linear or branched $C_1$ to $C_8$ alkenyl, linear or branched $C_1$ to $C_8$ alkynyl, $C_6$ to $C_{10}$ aryl, linear or branched $C_1$ to $C_6$ alkyl ether, silyl, trimethyl silyl, or linear or branched $C_1$ to $C_6$ alkyl-substituted silyl; $R^2$=H, linear or branched $C_1$ to $C_6$ alkyl, linear or branched $C_1$ to $C_8$ alkenyl, linear or branched $C_1$ to $C_8$ alkynyl, $C_6$ to $C_{10}$ aryl, linear or branched $C_1$ to $C_6$ alkyl ether, silyl, trimethyl silyl, or linear or branched $C_1$ to $C_6$ alkyl-substituted silyl; E is a group IVb element selected from the group consisting of Si or Ge.

A method of preparing the compounds having the structure $R^1X(CH_2)_nX(CH_2)_mXR^2E_kH_{(2k+1)}$, comprising:
a) contacting the reactants $R^1XH(CH_2)_nXH(CH_2)_mXHR^2$ and $HE_kH_{(2k+1)}$ in the presence of a transition metal catalyst forming a reaction mixture;
b) optionally adding a solvent to the reaction mixture;
c) maintaining the reaction mixture at a temperature between about 0° C. to about 300° C.;
d) allowing the reaction to proceed to form $R^1X(CH_2)_nX(CH_2)_mXR^2E_kH_{(2k+1)}$;
e) separating the $R^1X(CH_2)_nX(CH_2)_mXR^2E_kH_{(2k+1)}$ from the reaction mixture;
wherein the reaction temperature may vary during the synthesis and is maintained such that the temperature of the reaction mixture is not allowed to drop below about 0° C. and not exceed about 300° C.

A compound having the formula:

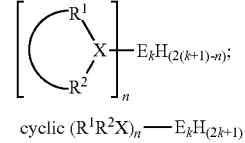

cyclic $(R^1R^2X)_n \cdot E_kH_{(2k+1)}$

Wherein n=1; k=1 to 6; X=P, As, Sb; $R^1$ and $R^2$ are independently selected from the group consisting of —CHR'—; —CHR'—CHR"—; —CHR'—CHR"—CHR'"—; =CH—; —CR'=CR"—; =CH—; —CHR'=CHR"—; and R', R", and R'" are independently selected from the group consisting of H, linear or branched $C_1$ to $C_6$ alkyl, linear or branched $C_1$ to $C_8$ alkenyl, linear or branched $C_1$ to $C_8$ alkynyl, $C_6$ to $C_{10}$ aryl, linear or branched $C_1$ to $C_6$ alkyl ether, silyl, trimethyl silyl, or linear or branched $C_1$ to $C_6$ alkyl-substituted silyl; and E is a group IVb element selected from the group consisting of Si or Ge.

A method of preparing the compounds having the structure cyclic $R^1R^2X\text{-}E_kH_{(2k+1)}$, comprising:
a) contacting the reactants cyclic $R^1R^2XH$ and $HE_kH_{(2k+1)}$, in the presence of a transition metal catalyst forming a reaction mixture; where the molar ratio of $HE_kH_{(2k+1)}$ to cyclic $R^1R^2XH$ is at least 3:1;
b) optionally adding a solvent to the reaction mixture;
c) maintaining the reaction mixture at a temperature between about 0° C. to about 300° C.;
d) allowing the reaction to proceed to form cyclic $R^1R^2X\text{-}E_kH_{(2k+1)}$;
e) separating the cyclic $R^1R^2X\text{-}E_kH_{(2k+1)}$) from the reaction mixture;
wherein the reaction mixture temperature may vary during the synthesis and is maintained such that the temperature of the reaction mixture is not allowed to drop below about 0° C. and not exceed about 300° C.

A compound having the formula:

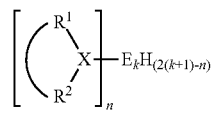

cyclic $R^1R^2X - E_kH_{(2k1-2)} - XR^1R^2$ cyclic

Wherein: X=P, As, Sb; n=1 or 2; k=1 to 6; $R^1$ and $R^2$ are independently selected from the group consisting of —CHR'—; —CHR'—CHR"—; —CHR'—CHR"—CHR'"—; =CH—; —CR'=CR"—; =CH—; —CHR'=CHR"—
and R', R", and R'" are independently selected from the group consisting of H, linear or branched $C_1$ to $C_6$ alkyl, linear or branched $C_1$ to $C_8$ alkenyl, linear or branched $C_1$ to $C_8$ alkynyl, $C_6$ to $C_{10}$ aryl, linear or branched $C_1$ to $C_6$ alkyl ether, silyl, trimethyl silyl, or linear or branched $C_1$ to $C_6$ alkyl-substituted silyl; and E is a group IVb element selected from the group consisting of Si or Ge.

A method of preparing the compounds having the structure comprising:

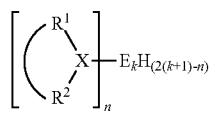

Cyclic $(R^1R^2X)_n - E_kH_{(2k1-2)}$ a) contacting the reactants cyclic $R_1R^2XH$ and $HE_kH_{(2k+1)}$, in the presence of a transition metal catalyst forming a reaction mixture; where the molar ratio of $HE_kH_{(2k+1)}$ to cyclic $R^1R^2XH$ is about 1:2;
b) optionally adding a solvent to the reaction mixture;
c) maintaining the reaction mixture at a temperature between about 0° C. to about 300° C.;
d) allowing the reaction to proceed to form cyclic $R^1R^2X\text{-}E_kH_{(2k1-2)}\text{—}XR^1R^2$ cyclic;
e) separating the cyclic $R^1R^2X\text{-}E_kH_{(2k1-2)}\text{—}XR^1R^2$ cyclic from the reaction mixture;
wherein the reaction temperature may vary during the synthesis and is maintained such that the temperature during the reaction is not allowed to drop below about 0° C. and not exceed about 300° C.

The following method describes the synthesis of aminosilanes comprising:
a) contacting the amine and silane reactants in the presence of a transition metal catalyst forming a reaction mixture;
b) optionally adding a solvent to the reaction mixture;
c) maintaining the reaction mixture at a temperature between about 0° C. to about 300° C.; d) allowing the reaction to proceed to form a product;
e) separating the product from the reaction mixture;

A method for preparing the compound having the formula:

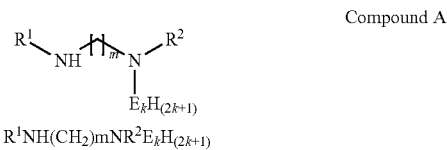

Compound A $R^1NH(CH_2)mNR^2E_kH_{(2k+1)}$ where one E is attached to one nitrogen; m=1 to 6; k=1 to 6; $R^1$ and $R^2$ are independently selected from the group consisting of linear or branched $C_1$ to $C_6$ alkyl, linear or branched $C_1$ to $C_8$ alkenyl, linear or branched $C_1$ to $C_8$ alkynyl, $C_6$ to $C_{10}$ aryl, linear or branched $C_1$ to $C_6$ alkyl ether, silyl, trimethyl silyl, or linear or branched $C_1$ to $C_6$ alkyl-substituted silyl; E is a group IVb element selected from the group consisting of Si or Ge:
a) contacting the reactants $R^1NH(CH_2)_mNHR^2$ and $HE_kH_{(2k+1)}$ in the presence of a transition metal catalyst forming a reaction mixture;
b) optionally adding a solvent to the reaction mixture;
c) maintaining the reaction mixture at a temperature between about 0° C. to about 300° C.; d) allowing the reaction to proceed to form $R^1NH(CH_2)_mNR^2E_kH_{(2k+1)}$;
e) separating the $R^1NH(CH_2)_mNR^2E_kH_{(2k+1)}$ from the reaction mixture;
wherein the reaction temperature may vary during the synthesis and is maintained such that the temperature of the reaction mixture is not allowed to drop below about 0° C. and not exceed about 300° C.

A method for preparing the compound having the formula:

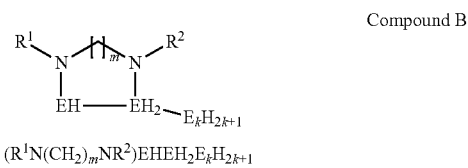

Compound B $(R^1N(CH_2)_mNR^2)EHEH_2E_kH_{2k+1}$ where one E is attached to 2 Nitrogens; m=1 to 6; $R^1$ and $R^2$ are independently selected from the group consisting of linear or branched $C_1$ to $C_6$ alkyl, linear or branched $C_1$ to $C_8$ alkenyl, linear or branched $C_1$ to $C_8$ alkynyl, $C_6$ to $C_{10}$ aryl, linear or branched $C_1$ to $C_6$ alkyl ether, silyl, trimethyl silyl, or linear or branched $C_1$ to $C_6$ alkyl-substituted silyl; E is a group IVb element selected from the group consisting of Si or Ge:
a) contacting the reactants $R^1N(CH_2)_mNHR^2$ and $HE_2H_3E_kH_{2k+1}$ in the presence of a transition metal catalyst forming a reaction mixture;
b) optionally adding a solvent to the reaction mixture;
c) maintaining the reaction mixture at a temperature between about 0° C. to about 300° C.;

d) allowing the reaction to proceed to form $R^1N(CH_2)_m NR^22EH_3E_kH_{2k+1}$;
e) separating the product $R^1N(CH_2)_mNR^22EH_3E_kH_{2k+1}$ from the reaction mixture;
wherein the reaction mixture temperature may vary during the synthesis and is maintained such that the temperature of the reaction mixture is not allowed to drop below about 0° C. and not exceed about 300° C.

A method for preparing the compound having the formula:

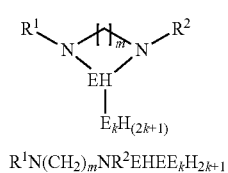

Compound C $R^1N(CH_2)_mNR^2EHEE_kH_{2k+1}$ where one E is attached to 1 Nitrogen; m=1 to 6; $R^1$ and $R^2$ are independently selected from the group consisting of linear or branched $C_1$ to $C_6$ alkyl, linear or branched $C_1$ to $C_8$ alkenyl, linear or branched $C_1$ to $C_8$ alkynyl, $C_6$ to $C_{10}$ aryl, linear or branched $C_1$ to $C_6$ alkyl ether, silyl, trimethyl silyl, or linear or branched $C_1$ to $C_6$ alkyl-substituted silyl; E is a group IVb element selected from the group consisting of Si or Ge:
a) contacting the reactants $R^1N(CH_2)_mNHR^2$ and $HEH_2E_kH_{2k+1}$ in the presence of a transition metal catalyst forming a reaction mixture;
b) optionally adding a solvent to the reaction mixture;
c) maintaining the reaction mixture at a temperature between about 0° C. to about 300° C.;
d) allowing the reaction to proceed to form $R^1N(CH_2)_m NR^2EHE_kH_{2k+1}$;
e) separating the product $R^1N(CH_2)_mNR^2EHE_kH_{2k+1}$ from the reaction mixture;
wherein the reaction mixture temperature may vary during the synthesis and is maintained such that the temperature of the reaction mixture is not allowed to drop below about 0° C. and not exceed about 300° C.

A method for preparing the compound having the formula:

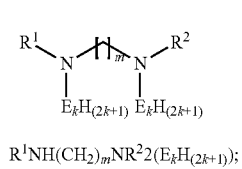

Compound D $R^1NH(CH_2)_mNR^22(E_kH_{(2k+1)})$;

where m=1 to 6; k=1 to 6; $R^1$ and $R^2$ are independently selected from the group consisting of linear or branched $C_1$ to $C_6$ alkyl, linear or branched $C_1$ to $C_8$ alkenyl, linear or branched $C_1$ to $C_8$ alkynyl, $C_6$ to $C_{10}$ aryl, linear or branched $C_1$ to $C_6$ alkyl ether, silyl, trimethyl silyl, or linear or branched $C_1$ to $C_6$ alkyl-substituted silyl; E is a group IVb element selected from the group consisting of Si or Ge:
a) contacting the reactants $R^1NH(CH_2)_mNHR^2$ and $HE_kH_{(2k+1)}$, in the presence of a transition metal catalyst forming a reaction mixture; where the molar ratio of $HE_kH_{(2k+1)}$ to $R^1NH(CH_2)_nNH(CH_2)_mNHR^2$ is at least 3:1;
b) optionally adding a solvent to the reaction mixture;
c) maintaining the reaction mixture at a temperature between about 0° C. to about 300° C.;
d) allowing the reaction to proceed to form $R^1NH(CH_2)_m NR^22(E_kH_{(2k+1)})$;
e) separating the product $R^1NH(CH_2)_mNR^22(E_kH_{(2k+1)})$ from the reaction mixture;
wherein the reaction temperature may vary during the synthesis and is maintained such that the temperature of the reaction mixture is not allowed to drop below about 0° C. and not exceed about 300° C.

Formation of monosubstituted compounds A, B and C is favored over formation of bis-substituted compound D by decreasing the $E_kH_{2k+2}$/Diamine ratio. However, formation of compounds A, B and C may be simultaneous and mixtures with different molar ratios of the three compounds will be synthesized. A/B/C molar ratios will vary depending on the nature of $R^1$ and $R^2$ groups and the length of the —$CH_2$— chain (value of m) as well as on the reaction conditions such as temperature, reaction time or catalyst. Bulkier R groups and longer chains are expected to favor the formation of A, whereas chains with m=1 to 3 are expected to favor the formation of compounds B and C.

A method for preparing the compound having the formula:

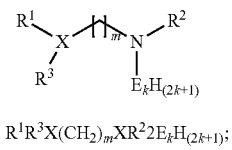

$R^1R^3X(CH_2)_mXR^22E_kH_{(2k+1)}$;

where X=P, As, Sb; m=1 to 6; k=1 to 6; $R^1$, $R^2$ and $R^3$ are independently selected from the group consisting of H, linear or branched $C_1$ to $C_6$ alkyl, linear or branched $C_1$ to $C_8$ alkenyl, linear or branched $C_1$ to $C_8$ alkynyl, $C_6$ to $C_{10}$ aryl, linear or branched $C_1$ to $C_6$ alkyl ether, silyl, trimethyl silyl, or linear or branched $C_1$ to $C_6$ alkyl-substituted silyl; E is a group IVb element selected from the group consisting of Si or Ge comprising:
a) contacting the reactants $R^1R^3X(CH_2)mXHR^2$ and $HE_kH_{(2k+1)}$ in the presence of a transition metal catalyst forming a reaction mixture;
b) optionally adding a solvent to the reaction mixture;
c) maintaining the reaction mixture at a temperature between about 0° C. to about 300° C.;
d) allowing the reaction to proceed to form $R^1R^3X(CH_2) mXR^2E_kH_{(2k+1)}$;
e) separating the $R^1R^3X(CH_2)mXR^2E_kH_{(2k+1)}$ from the reaction mixture;
wherein the reaction temperature may vary during the synthesis and is maintained such that the temperature of the reaction mixture is not allowed to drop below about 0° C. and not exceed about 300° C.

A method for preparing the compound having the formula:

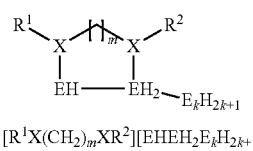

$[R^1X(CH_2)_mXR^2][EHEH_2E_kH_{2k+1}]$ where X=P, As, Sb; m=1 to 6; k=3 to 6; $R^1$ is selected from the group consisting of H, linear or branched $C_1$ to $C_6$ alkyl, linear or branched $C_1$ to $C_8$ alkenyl, linear or branched $C_1$ to $C_8$ alkynyl, $C_6$ to $C_{10}$ aryl, linear or branched $C_1$ to $C_6$ alkyl ether, silyl, trimethyl silyl, or linear or branched $C_1$ to $C_6$ alkyl-substituted silyl; $R^2$ is selected from the group consisting of H, linear or branched $C_1$ to $C_6$ alkyl, linear or branched $C_1$ to $C_8$ alkenyl, linear or branched $C_1$ to $C_8$ alkynyl, $C_6$ to $C_{10}$ aryl, linear or branched $C_1$ to $C_6$ alkyl ether, silyl, trimethyl silyl, or linear or branched $C_1$ to $C_6$ alkyl-substituted silyl; E is a group IVb element selected from the group consisting of Si or Ge comprising:
a) contacting the reactants $R^1X(CH_2)_mXHR^2$ and $H_3EH_2E$-$E_kH_{2k+1}$ in the presence of a transition metal catalyst forming a reaction mixture;
b) optionally adding a solvent to the reaction mixture;
c) maintaining the reaction mixture at a temperature between about 0° C. to about 300° C.;
d) allowing the reaction to proceed to form $[R^1X(CH_2)_m XR^2][EHEH_2E_kH_{2k+1}]$;
e) separating the product $[R^1X(CH_2)_mXR^2][EHEH_2E_k H_{2k+1}]$ from the reaction mixture;
wherein the reaction mixture temperature may vary during the synthesis and is maintained such that the temperature of the reaction mixture is not allowed to drop below about 0° C. and not exceed about 300° C. comprising:

A method for preparing the compound having the formula comprising:

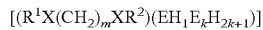

[$(R^1X(CH_2)_mXR^2)(EH_1E_kH_{2k+1})$]

where X=P, As, Sb; m=1 to 5; $R^1$ and $R^2$ are independently selected from the group consisting of linear or branched $C_1$ to $C_6$ alkyl, linear or branched $C_1$ to $C_8$ alkenyl, linear or branched $C_1$ to $C_8$ alkynyl, $C_6$ to $C_{10}$ aryl, linear or branched $C_1$ to $C_6$ alkyl ether, silyl, trimethyl silyl, or linear or branched $C_1$ to $C_6$ alkyl-substituted silyl comprising:
a) contacting the reactants $R^1X(CH_2)_mXHR^2$ and $HEH_2E_kH_{2k+1}$ in the presence of a transition metal catalyst forming a reaction mixture;
b) optionally adding a solvent to the reaction mixture;
c) maintaining the reaction mixture at a temperature between about 0° C. to about 300° C.;
d) allowing the reaction to proceed to form $R^1X(CH_2)_m XR^2EHE_kH_{2k+1}$;
e) separating the product $R^1X(CH_2)_mXR^2EHE_kH_{2k+1}$ from the reaction mixture;
wherein the reaction mixture temperature may vary during the synthesis and is maintained such that the temperature of the reaction mixture is not allowed to drop below about 0° C. and not exceed about 300° C.

A method for preparing the compound having the formula comprising:

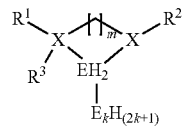

[$(R_1R^3X(CH_2)_m\!=\!XR^2)(EH_2E_kH_{2k+1})$]

where X=P, As, Sb; m=1 to 5; $R^1$, $R^2$ and $R^3$ are independently selected from the group consisting of linear or branched $C_1$ to $C_6$ alkyl, linear or branched $C_1$ to $C_8$ alkenyl, linear or branched $C_1$ to $C_8$ alkynyl, $C_6$ to $C_{10}$ aryl, linear or branched $C_1$ to $C_6$ alkyl ether, silyl, trimethyl silyl, or linear or branched $C_1$ to $C_6$ alkyl-substituted silyl, or branched $C_1$ to $C_6$ alkyl-substituted silyl comprising:

a) contacting the reactants $R^1R^3X(CH_2)_mXHR^2$ and $HEH_2E_kH_{2k+1}$ in the presence of a transition metal catalyst forming a reaction mixture;
b) optionally adding a solvent to the reaction mixture;
c) maintaining the reaction mixture at a temperature between about 0° C. to about 300° C.;
d) allowing the reaction to proceed to form $R^1R^3X(CH_2)_m XHR^2EH_2E_kH_{2k+1}$;
e) separating the product $R^1R^3X(CH_2)_mXHR^2EH_2E_kH_{2k+1}$ from the reaction mixture;
wherein the reaction mixture temperature may vary during the synthesis and is maintained such that the temperature of the reaction mixture is not allowed to drop below about 0° C. and not exceed about 300° C.

The term "maintaining . . . temperature" as used herein means heating or cooling as required to produce a temperature within the specified minimum and maximum temperature. The order of addition of amine and silane to the reaction vessel may be either amine first or silane first. When the starting materials are halogen free, the products will be halogen and amino halogen free.

The following method describes a method for the synthesis of diisopropylaminodisilane comprising:
a) contacting the reactants diisopropylamine and disilane in the presence of a transition metal catalyst forming a reaction mixture;
b) optionally adding a solvent to the reaction mixture;
c) heating the reaction mixture to a temperature between about 75° C. to about 200° C.;
d) allowing the reaction to proceed;
e) separating the diisopropylaminodisilane from the reaction mixture.

Heterogeneous catalysts suitable in the present invention include transition metal catalysts and rare earth elements. Catalysts are selected from the group consisting of: Sc, Ti, V, Cr, Mn, Fe, Co, Ni, Cu, Zn, Y, Zr, Nb, Mo, Tc, Ru, Rh, Pd, Ag, Cd, La, Hf, Ta, W, Re, Os, Ir, Pt, Au, Hg, Yb and U. Preferred catalysts are selected from the group consisting of Ru, Pd, Rh, Ir, Fe, Ni, Pt, Cr, Cu and Au. More preferred catalysts are selected from the group consisting of Rh, Pd, Ru and Pt. A most preferred catalyst is Ru and Ru on carbon. An additional preferred catalyst is Pd on MgO.

Catalysts of the present invention are preferably affixed to a support. The support is a solid with a high surface area. Typical support materials include but are not limited to: alumina, MgO, zeolites, carbon, Monolith cordierite, diatomaceous earth, silica gel, silica/alumina, ZrO and $TiO_2$. Preferred supports are carbon, alumina, silica and MgO. A more preferred support is carbon. Supports have a BET surface area ranging between about 1 $m^2/g$ to about 3,000 $m^2/g$. A preferred range is about 100 $m^2/g$ to about 2,000 $m^2/g$. Metal loading of the catalyst ranges between about 0.01 weight percent to about 50 weight percent. A preferred range is about 0.5 weight percent to about 20 weight percent. A more preferred range is about 0.5 weight percent to about 10 weight percent. Catalysts requiring activation may be activated by a number of known methods. Heating the catalyst under vacuum is a preferred method. The catalyst may be activated before addition to the reaction vessel or in the reaction vessel prior adding the reactants.

The catalyst may contain a promoter. Promoters are substances which themselves are not catalysts, but when mixed in small quantities with the active catalysts increase their efficiency (activity and/or selectivity). Promoters are usually metals such as Mn, Ce, Mo, Li, Re, Ga, Cu, Ru, Pd, Rh, Ir, Fe, Ni, Pt, Cr, Cu and Au and/or their oxides. They can be added separately to the reactor vessel or they can be part of the catalysts themselves. For example, Ru/Mn/C (ruthenium on carbon promoted by manganese) or Pt/CeO2/Ir/SiO2 (Platinum on silica promoted by ceria and iridium). Some promoters can act as catalyst by themselves but their use in combination with the main catalyst can improve the main catalyst's activity. A catalyst may act as a promoter for other catalysts. In this context, the catalyst can be called a bimetallic (or polymetallic) catalyst. For example, Ru/Rh/C can be called either ruthenium and rhodium on carbon bimetallic catalyst or ruthenium on carbon promoted by rhodium. An active catalyst is a material that acts as a catalyst in a specific chemical reaction.

Catalysts may require activation which is typically carried out under vacuum and at elevated temperatures. Typically catalysts are activated at about 125° C. and at about −14 psig which is about 1 Torr. Activation conditions will vary somewhat by the catalyst selected. Conditions for activating the various catalysts are known in the art. Activated catalysts may be stored for future use. Catalysts of the present invention do not comprise a halogen.

When solvents are used in the present invention, solvents that are non-reactive with the reactants are selected. Solvents are anhydrous and do not deactivate (poison) the catalyst. A non-limiting list of such solvents include: alkanes such as $C_5$ to $C_{20}$ linear, branched or cyclic alkanes and mixtures thereof, alkenes such as 1-octadecene, cyclooctadiene and cyclohexene; chloroalkanes such as methylene chloride and ethylene chloride; arenes such as toluene, xylene, mesitylene and naftalene and heterocycles such as quinoline and pyridine and mixtures thereof. A preferred solvent is n-octadecane. Preferably, the solvent should be selected such that its boiling point differs from the boiling point of the product compound by about 10° C.

Inert gas used in the present invention is not reactive under the reaction conditions. A non-limiting list of inert gases includes: helium, argon and nitrogen. A preferred gas is helium.

An autoclave such as a Parr autoclave equipped with a mechanical stirred is a suitable reaction vessel. For monosubstituted silanes or germanes, the molar ratio of heterocompound to silane or germane at the start of the reaction is within the range of about 2 to about 0.2, preferable within the range of about 1 to about 0.3. For bis-disubstituted silanes or germanes, the molar ratio of heterocompound to silane or germane at the start of the reaction is within the range of about 5 to about 2.

The method for the synthesis of halogen and aminohalogen free diisopropylaminodisilane in example 1 comprises:
a) adding a catalyst to a reaction vessel;
b) applying dynamic vacuum to the reaction vessel;
c) heating the reaction vessel to activate the catalyst;
d) maintaining vacuum and temperature of activation until the catalyst has been activated;
e) cooling the reaction vessel room temperature;
f) filling the reaction vessel with an inert gas to a pressure of about one atmosphere;
g) adding diisopropylamine to the reaction vessel;
h) adding solvent to the reaction vessel;
i) cooling the reaction vessel to a temperature between about −78° C. to about −140° C.;
j) adding disilane to the reactor forming a reaction mixture;
k) heating the reactor to a temperature between about 75° C. to about 200° C.;
l) stirring the heated reaction mixture;
m) monitoring the pressure in the reactor vessel until the pressure stops increasing;
n) cooling the reactor to about room temperature;
o) capturing volatiles in a cryotrap cooled to a temperature between about −140° C. to about −196° C.
p) monitoring the pressure in the reactor vessel until the pressure stops decreasing; and
q) recovering diisopropylaminodisilane from the reactor vessel.

Steps b to e are omitted if the catalyst of step a) is activated or does not require activation.

Recovery of the diisopropylaminodisilane can be carried out by distillation directly from the reactor vessel. The catalyst can be recycled for subsequent batches.

The term cryotrapping means condensing a gaseous material in a cryotrap.

Example 1

Synthesis of diisopropylaminodisilane "DIPADS"

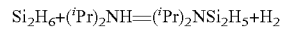

DIPADS (diisopropylaminodisilane also known as N,N-diisopropyl, N-disilylamine) was synthesized in a pressurized reactor vessel by the reaction between disilane and diisopropylamine catalyzed by commercially available Ruthenium on carbon in n-octadecane as a solvent: A 0.3 L autoclave (reaction vessel) equipped with a mechanical stirrer, a thermocouple, a pressure gauge and a pressure transducer and 3 metering valves, FIG. 1, was charged with 6 g (0.003 mmol of ruthenium) of 5% weight ruthenium on carbon catalyst. The reactor was then heated under dynamic vacuum at 125° C. for 3 hr. activating the catalyst. After cooling down to room temperature, the reactor was filled with helium at 1 atmosphere ("atm") pressure, sealed and disconnected from the manifold. Inside a glove box, 20.7 g (0.205 mol) of diisopropylamine and 75 g of n-octadecane were added to the reactor. Then, the reactor was taken out from the glove box and reconnected to the manifold and it was cooled down to −130° C. in a liquid nitrogen bath. 30 g (0.453 mol) of disilane were transferred to the reactor through the manifold. The reactor was then heated up to 150° C. After stirring at 400 rpm for 27 hr, pressure increased about 160 psi. Then, the reactor was cooled down to RT. Volatiles were cryotrapped in a stainless steel lecture bottle ("SSLB"). The reaction vessel pressure dropped to 45 Torr. The diisopropyoaminodisilane was recovered from the reaction vessel. The resulting solution contained 10% (9.9 g) of DIPADS. The non-isolated yield was 30%.

The term "non-isolated yield" means the yield is determined by weighing the reaction crude and estimating the amount of product by its chromatogram. The term "isolated yield" means the product was purified and weighed with the percent yield being determined by the percent of theoretical the amount weighed represents.

A solvent free method for the synthesis of chlorine free diisopropylaminodisilane for example 2 comprises:
a) adding a catalyst to a reaction vessel;
b) applying dynamic vacuum to the reaction vessel;
c) heating the reaction vessel to activate the catalyst;
d) maintaining vacuum and temperature of activation until the catalyst is activated;
e) cooling the reaction vessel to about room temperature;
f)) filling the reaction vessel with an inert gas to a pressure of about one atmosphere;
g) adding diisopropylamine to the reaction vessel;
h) cooling the reaction vessel to a temperature between about −78° C. and about −140° C.;
i) adding disilane to the reaction vessel forming a reaction mixture;
j) heating the reaction vessel to a temperature between about 75° C. to about 200° C.;

k) stirring the heated reaction mixture;
l) monitoring the pressure in the reaction vessel until the pressure stops increasing;
m) cooling the reaction vessel to about room temperature;
n) capturing volatiles in a cryotrap cooled to a temperature between about −140° C. to about −196° C.;
o) monitoring the pressure in the reactor vessel until the pressure stops decreasing; and
p) recovering the diisopropyoaminodisilane from the reactor vessel.
Steps b to e are omitted if the catalyst of step a) is activated.

Example 2

The solvent free synthesis of chlorine and aminochlorine free DIPADS in a pressurized reactor from disilane and diisopropylamine catalyzed by commercially available Ruthenium on carbon. A 0.3 L autoclave equipped with a mechanical stirrer, a thermocouple, a pressure gauge and a pressure transducer and 3 metering valves was charged with 6 g (0.003 mmol of ruthenium) of 5% weight ruthenium on carbon catalyst. The reactor was then heated under dynamic vacuum at 125° C. for 3 hr. After cooling down to room temperature, the reactor was filled with 1 atm. of helium, sealed and disconnected from the manifold. Inside a glove box, 20.7 (0.205 mol) of diisopropylamine were added. Then, the reactor was taken out from the glove box and reconnected to the manifold and it was cooled down to −130° C. in a liquid nitrogen bath. 30 g of disilane (0.453 mol) were transferred to the reactor through the manifold. The reactor was then heated up to 150° C. After stirring at 400 rpm for 24 hr, pressure increased around 100 psi. Then, the reactor was cooled down to RT. Volatiles were cryotrapped in a SSLB. The reaction vessel pressure dropped to 45 Torr. The resulting solution in the reactor vessel contained 65% (17 g) of DIPADS. The diisopropyoaminodisilane was recovered from the reactor vessel. The non-isolated yield was 52%.

The following method for the synthesis of compounds having silicon-heteroatom bonds without the formation of halogen salt by products has been developed. Reactants such as silane and phosphine are combined in the presence of a catalyst and heated to produce halogen free trisilylphosphine. The general reaction is given in the following equation:

$$PH_3 + 3SiH_4 = P(SiH_3)_3 + 3H_2$$

The reaction may be carried out in a solvent or without a solvent.

Example 3

Synthesis of trisilylphosphine: $PH_3 + 3SiH_4 = P(SiH_3)_3 + 3H_2$

A method for the synthesis of trisilylphosphine for example 3 comprises:
a) adding a catalyst to a reaction vessel;
b) applying dynamic vacuum to the reaction vessel;
c) heating the reaction vessel to activate the catalyst;
d) maintaining vacuum and temperature of activation until the catalyst is activated;
e) cooling the reaction vessel to about room temperature;
f) filling the reaction vessel with an inert gas to a pressure of about one atmosphere;
g) cooling the reaction vessel to a temperature between about −78° C. to about −140° C.;
h) adding phosphine to the reaction vessel;
i) adding silane to the reactor;
j) heating the reactor to a temperature between about 75° C. to about 200° C.;
k) stirring the heated reaction mixture;
l) monitoring the pressure in the reactor vessel until the pressure stops increasing;
m) cooling the reactor to about room temperature;
n) capturing volatiles in a cryotrap cooled to a temperature between about −140° C. to about −196° C.;
o) monitoring the pressure in the reactor vessel until the pressure stops decreasing; and
p) recovering the trisilylphosphine from the reactor vessel.
Steps b to e are omitted if the catalyst of step a) is activated.

Recovery of the trisilylphosphine is carried out by distillation directly from the reactor vessel. The catalyst can be recycled for subsequent batches.

Example 3

A method for synthesizing chlorine free trisilylphosphine in a pressurized reactor from silane and phosphine catalyzed by commercially available Ruthenium on carbon would comprise. A 0.3 L autoclave equipped with a mechanical stirrer, a thermocouple, a pressure gauge and a pressure transducer and 3 metering valves is charged with 10 g (0.005 mol of ruthenium) of 5% weight ruthenium on carbon catalyst. The reactor is then heated under dynamic vacuum at 125° C. for 3 hr. After cooling down to room temperature, the reactor is filled with 1 atm. of helium then cooled down to −130° C. in the liquid nitrogen bath. 15 g (0.44 mol) of phosphine and 50 g (1.6 mol) of silane are transferred to the reactor through the manifold. The reactor is then heated up to 150° C. After stirring at 400 rpm for 23 hr, the reactor is cooled down to RT. Volatiles are cryotrapped in a SSLB. The reaction vessel pressure will drop to about 45 Torr. The trisilylphosphine is recovered from the reactor vessel.

The molar ratio of phosphine to silane at the start of the reaction is within the range of about 1:3 to about 1:9.

A method for the synthesis of halogen free tris-disilylamine, $(Si_2H_5)_3N$, for example 4 comprises:
a) adding a catalyst to a reaction vessel;
b) applying dynamic vacuum to the reaction vessel;
c) heating the reaction vessel to activate the catalyst;
d) maintaining vacuum and temperature of activation until the catalyst is activated;
e) cooling the reaction vessel to about room temperature;
f)) filling the reaction vessel with an inert gas to a pressure of about one atmosphere;
g) cooling the reaction vessel to a temperature between about −78° C. and about −140° C.;
h) adding ammonia to the reaction vessel;
i) adding disilane to the reactor;
j) heating the reactor to a temperature between about 75° C. to about 200° C.;
k) stirring the heated reaction mixture;
l) monitoring the pressure in the reaction vessel until the pressure stops increasing;
m) cooling the reactor to about room temperature;
n) capturing volatiles in a cryotrap cooled to a temperature between about −140° C. to about −196° C.;
o) monitoring the pressure in the reactor vessel until the pressure stops decreasing; and
p) recovering the tris-disilylamine from the reactor vessel.
Steps b to e are omitted if the catalyst of step a is activated.

Example 4

Synthesis of halogen free tris-disilylamine, $3Si_2H_6 + NH_3 = (Si_2H_5)_3N + 3H_2$ A method for synthesizing halogen free tris-disilylamine $(Si_2H_5)_3N$ in a pressurized reactor from disilane and ammonia catalyzed by commercially available Ruthenium on carbon would comprise. A 0.3 L autoclave equipped with a mechanical stirrer, a thermocouple, a pressure gauge and a pressure transducer and 3 metering valves is charged with 17 g (0.0085 mol of ruthenium) of 5% weight ruthenium on carbon catalyst. The reactor is then heated under dynamic vacuum at 125° C. for 3 hr. After cooling down to room temperature, the reactor is filled with 1 atm. of helium then cooled down to −130 C. in a liquid nitrogen bath. 10 g (0.588 mol) of ammonia and 150 g (2.41 mol) of disilane are transferred to the reactor through the manifold. The reactor is then heated up to 150° C. After stirring at 400 rpm for 23 hr, the reactor is cooled down to RT. Volatiles are cryotrapped in a SSLB. The reaction vessel pressure will drop to about 45 Torr. The tris-disilylamine is recovered from the reactor vessel.

The molar ratio of amine to disilane at the start of the reaction was within the range of about 1:3 to about 1:5.

A solvent free method for the synthesis of halogen free diisopropylaminotrisilane (DIPATS) for example 5 comprises:
a) adding a catalyst to a reaction vessel;
b) applying dynamic vacuum to the reaction vessel;
c) heating the reaction vessel to activate the catalyst;
d) maintaining vacuum and temperature of activation until the catalyst is activated;
e) cooling the reaction vessel to about room temperature;
f)) filling the reaction vessel with an inert gas to a pressure of about one atmosphere;
g) adding diisopropylamine to the reaction vessel;
h) cooling the reaction vessel to a temperature between about −78° C. and about −140° C.;
i) adding trisilane to the reactor;
j) heating the reactor to a temperature between about 75° C. to about 200° C.;
k) stirring the heated reaction mixture;
l) monitoring the pressure in the reactor vessel until the pressure stops increasing;
m) cooling the reactor to about room temperature;
n) capturing volatiles in a cryotrap cooled to a temperature between about −140° C. to about −196° C.;
o) monitoring the pressure in the reactor vessel until the pressure stops decreasing; and
p) recovering the diisopropyoaminotrisilane from the reactor vessel.

Steps b to e are omitted if the catalyst of step a) is activated.

Example 5

Synthesis of $Si_3H_8 + (^iPr)_2NH = (^iPr)_2NSi_3H_7 + H_2$

A method for synthesizing halogen free diisopropylaminotrisilane (DIPATS) in a pressurized reactor from trisilane and diisopropylamine catalyzed by commercially available Ruthenium on carbon comprises. A 0.3 L autoclave equipped with a mechanical stirrer, a thermocouple, a pressure gauge and a pressure transducer and 3 metering valves was charged with 6 g (0.003 mmol of ruthenium) of 5% weight ruthenium on carbon catalyst. The reactor was then heated under dynamic vacuum at 125° C. for 3 hr. After cooling down to room temperature, the reactor was filled with 1 atm. of helium, sealed and disconnected from the manifold and placed in a glove box. Inside the glove box, 20.7 (0.205 mol) of diisopropylamine was added. Then, the reactor was taken out from the glove box and reconnected to the manifold and cooled down to −130° C. in a liquid nitrogen bath. 40 g of trisilane (0.433 mol) was transferred to the reactor through the manifold. The reactor was then heated up to 100° C. After stirring at 400 rpm for 23 hr, the reactor was cooled down to RT (room temperature). Volatiles were cryotrapped in a SSLB (stainless steel lecture bottle). The reaction vessel pressure dropped to 20 Torr. The diisopropylaminotrisilane was recovered from the reactor vessel. The reaction solution contained 11.49 g of DIPATS. The non-isolated yield was 29%.

Monosubstituted and disubstituted heterocyclic aminotrisilanes can be prepared by the methods described herein. Equation 2 representents monosubstituted heterocyclic aminosilanes and equation 3 represents disubstituted hetrocyclic aminosilanes.

$$Si_3H_8 + R^4NH = R^4NSi_3H_7 + H_2 \qquad 2.$$

$$Si_3H_8 + 2R^4NH = (R^4N)_2Si_3H_6 + 2H_2 \qquad 3.$$

Where $R^4$ is a cyclic secondary amine such as aziridine, azetidine, piperidine, pyrrolidine, pyrrole, imidazole, pyrazole and indole.

Equations 2 and 3 above describe the reaction to form monosubstituted and disubstituted heterocyclic trisilanes respectively. Monosubstituted compounds are shown in Table 1. Disubstituted trisilanes would have the second aminoheterocyclic group bonded to the third Si atom as in the disubstituted examples in Table 1.

Disubstituted aminotrisilanes are formed as shown in equation 4.

$$R^1Si_3H_7 + 2R^2R^3NH = R^2R^3NSi_3H_6NR^2R^3 + 2H_2 \qquad 4.$$

Where $R^1$=H and $R^2$=H, linear or branched $C_1$ to $C_6$ alkyl, linear or branched $C_1$ to $C_8$ alkenyl, linear or branched $C_1$ to $C_8$ alkynyl, $C_6$ to $C_{10}$ aryl, linear or branched $C_1$ to $C_6$ alkyl ether, silyl, trimethyl silyl, or linear or branched $C_1$ to $C_6$ alkyl-substituted silyl and $R^3$ is H, linear or branched $C_1$ to $C_6$ alkyl, linear or branched $C_1$ to $C_8$ alkenyl, linear or branched $C_1$ to $C_8$ alkynyl, $C_6$ to $C_{10}$ aryl, linear or branched $C_1$ to $C_6$ alkyl ether, silyl, trimethyl silyl, or linear or branched $C_1$ to $C_6$ alkyl-substituted silyl. Non-limiting examples of aminotrisilanes are shown in Table 1.

TABLE 1

Aminotrisilanes

| Monosubtituted | | Disubstituted | | |
|---|---|---|---|---|
|  | | 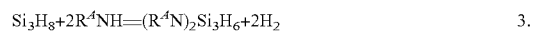 | | |
| $R^1$ | $R^2$ | $R^1$ | $R^2$ | Heterocyclic |
| Me | H | Me | H |  |
| Me | Me | Me | Me | |

TABLE 1-continued

Aminotrisilanes

| Monosubstituted | | Disubstituted | | Heterocyclic |
|---|---|---|---|---|
| $H_3Si-SiH_2-SiH_2-NR^1R^2$ | | $R^2R^1N-SiH_2-SiH_2-SiH_2-NR^1R^2$ | | |
| R$^1$ | R$^2$ | R$^1$ | R$^2$ | |
| Me | Et | Me | Et | 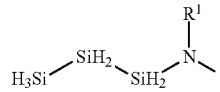 |
| Me | Pr | Me | Pr | |
| Me | Bu | Me | Bu | |
| Et | H | Et | H | 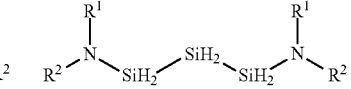 |
| Et | Pr | Et | Pr | |
| Et | Bu | Et | Bu | |
| Pr | H | Pr | H | 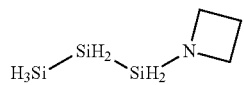 |
| Pr | Pr | Pr | Pr | |
| Pr | Bu | Pr | Bu | |
| Bu | H | Bu | H | 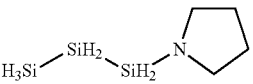 |
| Bu | Bu | Bu | Bu | |
| $^i$Pr | H | $^i$Pr | H | |
| $^i$Pr | Me | $^i$Pr | Me | 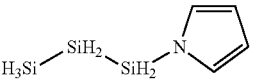 |
| $^i$Pr | Et | $^i$Pr | Et | |
| $^i$Pr | Pr | $^i$Pr | Pr | |
| $^i$Pr | $^i$Pr | $^i$Pr | $^i$Pr | 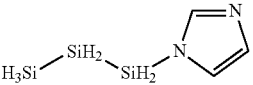 |
| $^i$Pr | Bu | $^i$Pr | Bu | |
| Ph | H | Ph | H | |

A solvent free method for the synthesis of chlorine free diisopropylaminosilane for example 6 comprises:

a) adding a catalyst to a reaction vessel;
b) applying dynamic vacuum to the reaction vessel;
c) heating the reaction vessel to activate the catalyst;
d) maintaining vacuum and temperature of activation until the catalyst is activated;
e) cooling the reaction vessel to about room temperature;
f)) filling the reaction vessel with an inert gas to a pressure of about one atmosphere;
g) adding diisopropylamine to the reaction vessel;
h) cooling the reaction vessel to a temperature between about −78° C. and about −140° C.;
i) adding trisilane to the reactor;
j) heating the reactor to a temperature between about 75° C. to about 200° C.;
k) stirring the heated reaction mixture;
l) monitoring the pressure in the reactor vessel until the pressure stops increasing;
m) cooling the reactor to about room temperature;
n) capturing volatiles in a cryotrap cooled to a temperature between about −140° C. to about −196° C.;
o) monitoring the pressure in the reactor vessel until the pressure stops decreasing; and
p) recovering the diisopropylaminosilane from the reactor vessel.

Steps b to e are omitted if the catalyst of step a) is activated or does not require activation.

Example 6

Synthesis of diisopropylaminosilane ($^i$Pr)$_2$NSiH$_3$ ($^i$Pr)$_2$NH+SiH$_4$=($^i$Pr)$_2$NSiH$_3$+H$_2$ A method for synthesizing chlorine free diisopropylaminosilane (DIPAS) in a pressurized reactor from silane and diisopropylamine catalyzed by commercially available Ruthenium on carbon would comprise. A 0.3 L autoclave equipped with a mechanical stirrer, a thermocouple, a pressure gauge and a pressure transducer and 3 metering valves is charged with 6 g (0.003 mmol of ruthenium) of 5% weight ruthenium on carbon catalyst. The reactor is then heated under dynamic vacuum at 125° C. for 3 hr. After cooling down to room temperature, the reactor is filled with 1 atm. of helium, sealed and disconnected from the manifold and placed in a glove box. Inside the glove box, 20.7 (0.205 mol) of diisopropylamine is added. Then, the reactor is taken out from the glove box and reconnected to the manifold and it is cooled down to −130° C. in a liquid nitrogen bath. 20 g of trisilane (0.625 mol) are transferred to the reactor through the manifold. The reactor is then heated up to 150° C. After stirring at 400 rpm for 23 hr, the reactor is cooled down to RT. Volatiles are cryotrapped in a SSLB. The reaction vessel pressure will drop to about 45 Torr. The diisopropyoaminosilane is recovered from the reactor vessel.

A method for the synthesis of bis(diisopropylamino) disilane comprising:
a) adding an activated catalyst, diisopropylamine and disilane to a reaction vessel;
b) optionally adding a solvent to the reaction vessel;
c) heating the reaction vessel to a temperature between about 25° C. to about 300° C.;
d) allowing the reaction to proceed;
e) separating the non-reacted materials, by products and hydrogen from the bis(diisopropylamino)disilane; and
f) recovering the bis(diisopropylamino)disilane.

A method for the synthesis of $(R^2R^3N)_m\,SiR^4_{2-m}$—$SiR^5_{2-m}(NR^2R^3)$ wherein $R^2$=H, linear or branched $C_1$ to $C_6$ alkyl, linear or branched $C_1$ to $C_8$ alkenyl, linear or branched $C_1$ to $C_8$ alkynyl, $C_6$ to $C_{10}$ aryl, linear or branched $C_1$ to $C_6$ alkyl and $R_3$=H, linear or branched $C_1$ to $C_6$ alkyl, linear or branched $C_1$ to $C_8$ alkenyl, linear or branched $C_1$ to $C_8$ alkynyl, $C_6$ to $C_{10}$ aryl, linear or branched $C_1$ to $C_6$ alkyl and, $R_4$=H, linear or branched $C_1$ to $C_6$ alkyl, linear or branched $C_1$ to $C_8$ alkenyl, linear or branched $C_1$ to $C_8$ alkynyl, $C_6$ to $C_{10}$ aryl, linear or branched $C_1$ to $C_6$ alkyl and, $R_5$=H, linear or branched $C_1$ to $C_6$ alkyl, linear or branched $C_1$ to $C_8$ alkenyl, linear or branched $C_1$ to $C_8$ alkynyl, $C_6$ to $C_{10}$ aryl, linear or branched $C_1$ to $C_6$ alkyl and m=0, 1 or 2 comprising:
a) adding an activated catalyst, $R^2R^3NH$ and $HSiR^4_{2-m}$—$SiR^5_{2-m}H$ to a reaction vessel;
b) optionally adding a solvent to the reaction vessel;
c) heating the reaction vessel to a temperature between about 25° C. to about 300° C.;
d) allowing the reaction to proceed;
e) separating the non-reacted materials, by products and hydrogen from the product, and
f) recovering the product.

A method for the synthesis of compounds having germanium-heteroatom bonds without the formation of halogen salt by products has been developed. Reactants such as germane and phosphine are combined in the presence of an activated catalyst and heat to produce halogen free trigernanephosphine. The general reaction is given in the following equation:

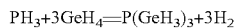
PH₃+3GeH₄=P(GeH₃)₃+3H₂

The reaction may be carried out in a solvent or without a solvent.
Synthesis of trigermanephosphine $P(GeH_3)_3$ is represented by the

Example 8

Synthesis of trisilylphosphine

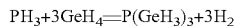
PH₃+3GeH₄=P(GeH₃)₃+3H₂

A method for the synthesis of trigermanephosphine comprising:
a) adding an activated catalyst, phosphine and germane to a reaction vessel;
b) optionally adding a solvent to the reaction vessel;
c) maintaining the reaction vessel to a temperature between about 25° C. to about 300° C.;
d) allowing the reaction to proceed;
e) separating the non-reacted materials, by products and hydrogen from the trigermanephosphine; and
f) recovering the trigermanephosphine.

A method for the synthesis of diisopropyoaminogermane comprising:
a) adding an activated catalyst, isopropylamine and germane to a reaction vessel;
b) optionally adding a solvent to the reaction vessel;
c) maintaining the reaction vessel to a temperature between about 25° C. to about 300° C.;
d) allowing the reaction to proceed;
e) separating the non-reacted materials, by products and hydrogen from the diisopropyoaminogermane; and
f) recovering the diisopropyoaminogermane.

Silylamidinates

A method for preparing the compound having the formula:

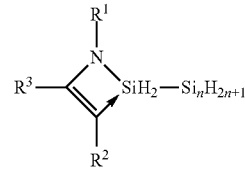

[(R₁N(CR³)=NR²)(SiH₂Si_nH_{2n+1})]

where n=1 to 5; $R^1$, $R^2$ and $R^3$ are independently selected from the group consisting of linear or branched $C_1$ to $C_6$ alkyl, linear or branched $C_1$ to $C_8$ alkenyl, linear or branched $C_1$ to $C_8$ alkynyl, $C_6$ to $C_{10}$ aryl, linear or branched $C_1$ to $C_6$ alkyl ether, silyl, trimethyl silyl, or linear or branched $C_1$ to $C_6$ alkyl-substituted silyl
a) contacting the reactants $R^1HN(CR^3)$=$NR^2$ (amidine) and $SiH_3Si_nH_{2n+1}$, in the presence of a transition metal catalyst forming a reaction mixture; where the molar ratio of $SiH_3Si_nH_{2n+1}$ to $R^1HN(CR^3)$=$NR^2$ is at least 1:1;
b) optionally adding a solvent to the reaction mixture;
c) maintaining the reaction mixture at a temperature between about 0° C. to about 300° C.;
d) allowing the reaction to proceed to form $[(R^1N(CR^3)$=$NR^2)(SiH_2Si_nH_{2n+1})]$;
e) separating the product $[(R^1N(CR^3)$=$NR^2)(SiH_2Si_nH_{2n+1})]$ from the reaction mixture;
wherein the reaction temperature may vary during the synthesis and is maintained such that the temperature of the reaction mixture is not allowed to drop below about 0° C. and not exceed about 300° C.

Example 7

The solvent free synthesis of chlorine and aminochlorine free N,N'-bis(isopropyl)ethanimidamidatodisilane in a pressurized reactor from disilane and N,N'-bis(isopropyl)ethanimidamide catalyzed by commercially available Ruthenium on carbon. A 0.3 L autoclave equipped with a mechanical stirrer, a thermocouple, a pressure gauge and a pressure transducer and 3 metering valves is charged with 6 g (0.003 mmol of ruthenium) of 5% weight ruthenium on carbon catalyst. The reactor is then heated under dynamic vacuum at 125° C. for 3 hr. After cooling down to room temperature, the reactor is filled with 1 atm. of helium, sealed and disconnected from the manifold. Inside a glove box, 29.1 g (0.205 mol) of N,N'-bis(isopropyl)ethanimidamide are added. Then, the reactor is taken out from the glove box and reconnected to the manifold and it is cooled down to −130° C. in a liquid nitrogen bath. 30 g of disilane (0.453 mol) are transferred to the reactor through the manifold. The reactor is then heated up to 100-150° C. The reaction mixture is stirred at about 400 rpm for about 2-24 hr, pressure increases to about 100 psi. Then, the reactor is cooled to RT. Volatiles are cryotrapped in a SSLB. The reaction vessel pressure drops to about 45 Torr. The N,N'-bis(isopropyl)ethanimidamidatosilane is recovered from the reactor vessel.

A method for preparing the compound having the formula:

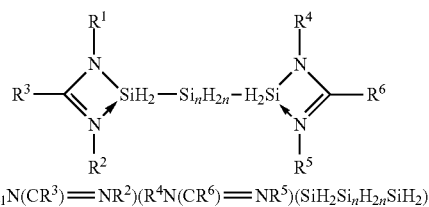

$[(R_1N(CR^3)=NR^2)(R^4N(CR^6)=NR^5)(SiH_2Si_nH_{2n}SiH_2)]$ where n=0 to 4; $R^1$, $R^2$, $R^3$, $R^4$, $R^5$, $R^6$ are independently selected from the group consisting of linear or branched $C_1$ to $C_6$ alkyl, linear or branched $C_1$ to $C_8$ alkenyl, linear or branched $C_1$ to $C_8$ alkynyl, $C_6$ to $C_{10}$ aryl, linear or branched $C_1$ to $C_6$ alkyl ether, silyl, trimethyl silyl, or linear or branched $C_1$ to $C_6$ alkyl-substituted silyl a) contacting the reactants $R^1HN(CR^3)=NR^2$ (amidine) and $SiH_3Si_nH_{2n}SiH_3$, in the presence of a transition metal catalyst forming a reaction mixture
b) optionally adding a solvent to the reaction mixture;
c) maintaining the reaction mixture at a temperature between about 0° C. to about 300° C.;
d) allowing the reaction to proceed to form $[(R^1N(CR^3)=NR^2)(SiH_2Si_nH_{2n}SiH_3)]$;
e) adding $R^4HN(CR^6)=NR^5$ to the reaction mixture
f) maintaining the reaction mixture at a temperature between about 0° C. to about 300° C.;
g) allowing the reaction to proceed to form $[(R^1N(CR^3)=NR^2)(R^4N(CR^6)=NR^5)(SiH_2Si_nH_{2n}SiH_2)]$;
h) separating the product $[(R^1N(CR^3)=NR^2)(R^4N(CR^6)=NR^5)(SiH_2Si_nH_{2n}SiH_2)]$ from the reaction mixture;
wherein the reaction temperature may vary during the synthesis and is maintained such that the temperature of the reaction mixture is not allowed to drop below about 0° C. and not exceed about 300° C.

If $R^1HN(CR^3)=NR^2$ is the same as $R^4HN(CR^6)=NR^5$, the product will be $[(R^1N(CR^3)=NR^2)_2(SiH_2Si_nH_{2n}SiH_2)]$.

The order of addition of the amidines may vary depending on the nature of the groups $R_1$, $R_2$, $R_3$, $R_4$, $R_5$ and $R_6$. The addition of the second amidine can be performed separately, therefore the silylamidinate $[(R^1N(CR^3)=NR^2)(SiH_2Si_nH_{2n}SiH_3)]$ can be isolated and/or purified and subsequently contacted with $R^4HN(CR^6)=NR^5$ in the presence of a transition metal catalyst to form $[(R^1N(CR^3)=NR^2)(R^4N(CR^6)=NR^5)(SiH_2Si_nH_{2n}SiH_2)]$.

Sequential amine addition for the synthesis of aminosilanes with two different amines having the formula

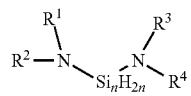

Comprising:
a) contacting the reactants $R^1R^2NH$ and $E_kH_{2(k+1)}$ in the presence of a transition metal catalyst forming a reaction mixture;
b) optionally adding a solvent to the reaction mixture;
c) maintaining the reaction mixture at a temperature between about 0° C. to about 300° C.;
d) allowing the reaction to proceed to form $(R^1R^2N)_{n1}E_kH_{(2(k+1)-n1)}$;
e) adding $R^3R^4NH$ to the reaction mixture;
f) maintaining the reaction mixture at a temperature between about 0° C. to about 300° C.;
g) allowing the reaction to proceed to form $(R^1R^2N)_{n1}(R^3R^4N)_{n2}E_kH_{(2(k+1)-n1-n2)}$;
h) separating the $(R^1R^2N)_{n1}(R^3R^4N)_{n2}E_kH_{(2(k+1)n1-n2)}$ from the reaction mixture;
wherein the reaction mixture temperature may vary during the synthesis and is maintained such that the temperature of the reaction mixture is not allowed to drop below about 0° C. and not exceed about 300° C.

The order of addition of the amines may vary depending on the nature of the groups $R_1$, $R_2$, $R_3$ and $R_4$. The addition of the second amine can be performed separately, therefore the aminosilane $(R^1R^2N)_{n1}E_kH_{(2(k+1)-n1)}$ can be isolated and/or purified and subsequently contacted with $R^3R^4NH$ in the presence of a transition metal catalyst to form $(R^1R^2N)_{n1}(R^3R^4N)_{n2}E_kH_{(2(k+1)-n1-n2)}$ Example 9

Diisopropylaminodiethylaminodisilane Synthesis

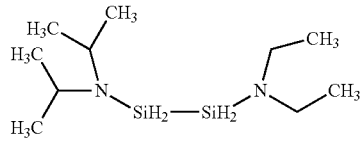

Diisopropylaminodiethylaminodisilane is synthesized in a pressurized reactor vessel by the reaction between disilane, diisopropylamine and diethylamine catalyzed by commercially available Ruthenium on carbon: A 0.3 L autoclave (reaction vessel) equipped with a mechanical stirrer, a thermocouple, a pressure gauge and a pressure transducer and 3 metering valves, as illustrated in FIG. 1, is charged with 6 g (0.003 mmol of ruthenium) of 5% weight ruthenium on carbon catalyst. The reactor is then heated under dynamic vacuum at 125° C. for 3 hr. activating the catalyst. After cooling to room temperature, the reactor is filled with helium at 1 atmosphere ("atm") pressure, sealed and disconnected from the manifold. Inside a glove box, 20.7 g (0.205 mol) of diisopropylamine is added to the reactor. The reactor is taken out from the glove box and reconnected to the manifold and it is cooled to −130° C. in a liquid nitrogen bath. 30 g (0.453 mol) of disilane are transferred to the reactor through the manifold. The reactor is heated to about 150° C. The reactor contents is stirred at about 400 rpm for about 5 hr, pressure in the reactor increases about 160 psi. The reactor is cooled to RT. Volatiles are cryotrapped in a stainless steel lecture bottle ("SSLB"). The reaction vessel pressure drops to about 45 Torr. The reactor is put back in the glove box and is opened. 15.0 g (0.205 mol) of diethylamine are added to the mixture. They reactor is then heated to temperatures varying from about 30° C. to about 150° C. The reactor is stirred at about 400 rpm for about 2-24 hr. the pressure increases to about 160 psi. Volatiles are cryotrapped in a stainless steel lecture bottle ("SSLB"). The reaction vessel pressure drops to about 25-45 Torr. The diisopropylaminodiethylaminodisilane is recovered from the reaction vessel.

The order of addition of amines may be reversed.

The aminosilanes of the present invention are used as precursors for vapor deposition methods. Disclosed herein are methods of using the disclosed precursors for vapor deposition methods. The disclosed methods provide for the use of the precursors for deposition of silicon-containing films. The disclosed methods may be useful in the manufacture of semiconductor, photovoltaic, LCD-TFT, or flat panel type devices. The method includes: introducing the vapor of the disclosed precursors into a reactor having at least one substrate disposed therein: and using a vapor deposition process to deposit at least part of the disclosed precursor onto the substrate to form a Si-containing layer.

The disclosed methods also provide for forming a bimetal containing layer on a substrate using a vapor deposition process and, more particularly, for deposition of $SiMN_x$ and $SiMO_x$ films wherein x is 0-4, and $SiMO_xN_y$ films, wherein x+y is 0 to 4 and M is a metal from the group Ta, Hf, Zr, Ti, Ni, Mn, Ge, B, Nb, Mg, Al, Sr, Y, Ba, Ca, As, Sb, Bi, Sn, Pb, Co, lanthanides (such as Er), or combinations thereof. The general $SiMO_x$, $SiMO_x$ or $SiMO_xN_y$ terminology covers various relative concentrations of Si and M in the range of Si/(Si+M) is about 5% to about 95%.

The disclosed methods of forming silicon-containing layers on substrates may be useful in the manufacture of semiconductor, photovoltaic, LCD-TFT, or flat panel type devices. The disclosed precursors may deposit Si-containing films using any vapor deposition methods known in the art. Examples of suitable vapor deposition methods include chemical vapor deposition (CVD) or atomic layer deposition (ALD). Exemplary CVD methods include thermal CVD, plasma enhanced CVD (PECVD), pulsed CVD (PCVD), low pressure CVD (LPCVD), sub-atmospheric CVD (SACVD) or atmospheric pressure CVD (APCVD), hot-wire CVD (HWCVD, also known as cat-CVD, in which a hot wire serves as an energy source for the deposition process, remote plasma CVD (RP-CVD) UV assisted CVD, flowable CVD (FCVD)), radicals incorporated CVD, and combinations thereof. Exemplary ALD methods include thermal ALD, plasma enhanced ALD (PEALD), spatial isolation ALD, hot-wire ALD (HWALD), radicals incorporated ALD, UV assisted ALD and combinations thereof. Super critical fluid deposition may also be used. The disclosed methods may also be used in the flowable PECVD deposition processes described in U.S. Pat. App. Pub. No. 2014/0051264 to Applied Materials, Inc., the contents of which is incorporated herein in its entirety. The deposition method is preferably ALD, spatial ALD, PE-ALD or flowable CVD (F-CVD).

The vapor of the precursor is introduced into a reaction chamber containing at least one substrate. The temperature and the pressure within the reaction chamber and the temperature of the substrate are held at conditions suitable for vapor deposition of at least part of the precursor onto the substrate. In other words, after introduction of the vaporized precursor into the chamber, conditions within the chamber are such that at least part of the vaporized precursor is deposited onto the substrate to form the silicon-containing film. A co-reactant may also be used to help in formation of the Si-containing layer. The co-reactant may be introduced simultaneously or separately sequentially from the precursors and is selected from $O_2$, $O_3$, O radicals and ions, NO, $N_2O$, $H_2O$, $H_2O_2$, $CO_2$, CO, carboxylic acid, formalin, alcohols, diols, $NH_3$, hydrazines (substituted or not, such as UDMH, terbutylhydrazine), amines (such as DMA, TMA, DEA, TEA, TB, $NH_2$), diamines, N radicals and ions, $H_2$ and mixtures thereof.

The reaction chamber may be any enclosure or chamber of a device in which deposition methods take place, such as, without limitation, a parallel-plate type reactor, a cold-wall type reactor, a hot-wall type reactor, a single-wafer reactor, a multi-wafer reactor, or other such types of deposition systems such as spatial ALD chambers, roll to roll ALD chambers. All of these exemplary reaction chambers are capable of serving as an ALD reaction chamber. The reaction chamber may be maintained at a pressure ranging from about 1 mTorr to about 760 Torr. In addition, the temperature within the reaction chamber may range from about 20° C. to about 600° C. One of ordinary skill in the art will recognize that the temperature may be optimized through mere experimentation to achieve the desired result.

The temperature of the reactor may be controlled by either controlling the temperature of the substrate holder, controlling the temperature of the reactor wall, or controlling the temperature of the substrate itself. Devices used to heat the substrate are known in the art. The reactor wall is heated to a sufficient temperature to obtain the desired film at a sufficient growth rate and with desired physical state and composition. A non-limiting exemplary temperature range to which the reactor wall may be heated includes from approximately 20° C. to approximately 600° C. When a plasma deposition process is utilized, the deposition temperature may range from approximately 20° C. to approximately 550° C. Alternatively, when a thermal process is performed, the deposition temperature may range from approximately 200° C. to approximately 600° C.

Alternatively, the substrate may be heated to a sufficient temperature to obtain the desired silicon-containing film at a sufficient growth rate and with desired physical state and composition. A non-limiting exemplary temperature range to which the substrate may be heated includes from 150° C. to 600° C. Preferably, the temperature of the substrate remains less than or equal to 500° C.

The type of substrate upon which the silicon-containing film will be deposited will vary depending on the final use intended. A substrate is generally defined as the material on which a process is conducted. The substrates may be any suitable substrate used in semiconductor, photovoltaic, flat panel, or LCD-TFT device manufacturing. Examples of suitable substrates include wafers, such as silicon, silica, glass, Ge, or GaAs wafers. The wafer may have one or more layers of differing materials deposited on it from a previous manufacturing step. For example, the wafers may include silicon layers (crystalline, amorphous, porous, etc.), silicon oxide layers, silicon nitride layers, silicon oxy nitride layers, carbon doped silicon oxide (SiCOH) layers, porous carbon doped silicon oxide layers, silicon carbo-nitride, hydrogenerated silicon carbide, or combinations thereof. Additionally, the wafers may include copper layers, tungsten layers or metal layers (for example platinum, palladium, nickel, rhodium, gold, Cobalt, germanium, antimony, tellurium, tin, ruthenium and their alloys). The wafers may include barrier layers, such as manganese, manganese oxide, nitrides of Ta, W, Ti, V, Zr, Hg, Nb, Mo, Mn and Ru. Nitride may be C-doped nitride. Plastic layers, such as poly(3,4-ethylenedioxythiophene)poly (styrenesulfonate) [PEDOT:PSS] may also be used. The film may be deposited over an organic film, such as a photoresist layer, an amorphous carbon layer, or a polyimide film. The layers may be planar or patterned. In some embodiments, the substrate may include layers of oxides which are used as dielectric materials in MIM, DRAM, RERAM, phase change RAM, or FeRam technologies (for example, Zr, Hg, Ti, Nb, Mo, Al, Ta, lanthanides, rare earths and mixed ternary or binaryoxides thereof) or from nitride-based films (for example, TaN) that are used as an adhesion barrier between copper and the low-k layer. The disclosed processes may deposit the silicon-containing layer directly on the wafer or directly on one or more than one (when patterned layers form the substrate) of the layers on top of the wafer. Furthermore, one of ordinary skill in the art will recognize that the terms "film" or "layer" used herein refer to a thickness of some material laid on or spread over a surface and that the surface may have 3D patterns or microstructures such as holes and trenches or a line. The deposition may be selective to specific areas on the substrate, or selective to certain exposed materials. For example, the growth may be inhibited on certain parts of the substrate covered with self aligned monolayers ("SAM"). Throughout the specification and claims, the wafer and any associated layers thereon are referred to as substrates.

The disclosed precursors may be supplied either in neat form or in a blend with a suitable solvent, such as toluene, ethyl benzene, xylene, mesitylene, decane, dodecane, octane, hexane, pentane, tertiary amines, tetrahydrofuran, ethylmethylketone, decalin, or others. The disclosed precursors may be present in varying concentrations in the solvent. For example, the resulting concentration may range from approximately 0.05 M to approximately 2 M.

The neat or blended precursors are introduced into a reactor in vapor form by conventional means, such as tubing and/or flow meters. The precursor in vapor form may be produced by vaporizing the neat or blended precursor solution through a conventional vaporization step such as, bubbling, vapor draw or by using a sublimator such as the one disclosed in PCT Publication WO2009/087609 to Xu et al. The neat or blended precursor may be fed in liquid state to a vaporizer where it is vaporized before it is introduced into the reactor (direct liquid injection). When present, the carrier gas may include, but is not limited to, Ar, He, $N_2$, or $H_2$ and mixtures thereof. The carrier gas and precursor are then introduced into the reactor as a vapor.

If necessary, the container may be heated to a temperature that permits the precursor to be in its liquid or solid phase and to have a sufficient vapor pressure. The container may be maintained at temperatures in the range of, for example, 0-150° C. Those skilled in the art recognize that the temperature of the container may be adjusted in a known manner to control the vapor pressure of the precursor vaporized and the concentration in the process chamber.

The film obtained by a vapor deposition method can be further treated by various methods such as annealing, reactive annealing, UV curing, e-beam curing and radical annealing. The film composition and structure can be significantly affected by this step.

It will be understood that many additional changes in the details, materials, steps, and arrangement of parts, which have been herein described and illustrated in order to explain the nature of the invention, may be made by those skilled in the art within the principle and scope of the invention as expressed in the appended claims. Thus, the present invention is not intended to be limited to the specific embodiments in the examples given above and/or the attached drawings.

Although the description above contains much specificity, these should not be construed as limiting the scope of the invention but as merely providing illustrations of some of the presently preferred embodiments of this invention. Various other embodiments and ramifications are possible within its scope. It will be understood that many additional changes in the details, materials, steps, and arrangement of parts, which have been herein described and illustrated in order to explain the nature of the invention, may be made by those skilled in the art within the principle and scope of the invention as expressed in the appended claims.

We claim:

1. A compound of formula:

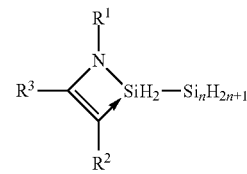

where n=1 to 5; $R^1$, $R^2$ and $R^3$ are independently selected from the group consisting of H, linear or branched $C_1$ to $C_6$ alkyl, linear or branched $C_1$ to $C_8$ alkenyl, linear or branched $C_1$ to $C_8$ alkynyl, $C_6$ to $C_{10}$ aryl, linear or branched $C_1$ to $C_6$ alkyl ether, silyl, trimethyl silyl, or linear or branched $C_1$ to $C_6$ alkyl-substituted silyl.

2. A method of preparing a compound according to claim 1, comprising the steps of:
a) contacting the reactants $R^1HN(CR^3)=NR^2$ (amidine) and $SiH_3Si_nH_{2n+1}$, in the presence of a transition metal catalyst forming a reaction mixture; where the molar ratio of $SiH_3Si_nH_{2n+1}$ to $R^1HN(CR^3)=NR^2$ is at least 1:1;
b) optionally adding a solvent to the reaction mixture;
c) maintaining the reaction mixture at a temperature between about 0° C. to about 300° C.;
d) allowing the reaction to proceed to form $[(R^1N(CR^3)=NR^2)(SiH_2Si_nH_{2n+1})]$; and
e) separating the product $[(R^1N(CR^3)=NR^2)(SiH_2Si_nH_{2n+1})]$ from the reaction mixture,
wherein the reaction temperature may vary during the synthesis and is maintained such that the temperature of the reaction mixture is not allowed to drop below about 0° C. and not exceed about 300° C.

3. A compound of formula:

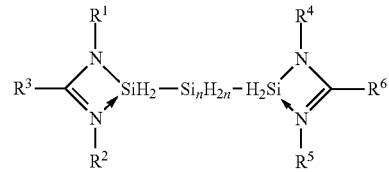

where n=0 to 4; $R^1$, $R^2$, $R^3$, $R^4$, $R^5$, $R^6$ are independently selected from the group consisting of H, linear or branched $C_1$ to $C_6$ alkyl, linear or branched $C_1$ to $C_8$ alkenyl, linear or branched $C_1$ to $C_8$ alkynyl, $C_6$ to $C_{10}$ aryl, linear or branched $C_1$ to $C_6$ alkyl ether, silyl, trimethyl silyl, or linear or branched $C_1$ to $C_6$ alkyl-substituted silyl.

4. A method of preparing a compound according to claim 3, comprising the steps of:
a) contacting the reactants $R^1HN(CR^3)=NR^2$ (amidine) and $SiH_3Si_nH_{2n}SiH_3$, in the presence of a transition metal catalyst forming a reaction mixture where the molar ratio of $R^1HN(CR^3)=NR^2$ to $SiH_3Si_nH_{2n}SiH_3$ is about 1:1 to about 5:1;

b) optionally adding a solvent to the reaction mixture;

c) maintaining the reaction mixture at a temperature between about 0° C. to about 300° C.;

d) allowing the reaction to proceed to form $[(R^1N(CR^3)=NR^2)(SiH_2Si_nH_{2n}SiH_3)]$;

e) adding $R^4HN(CR^6)=NR^5$ to the reaction mixture;

f) maintaining the reaction mixture at a temperature between about 0° C. to about 300° C.;

g) allowing the reaction to proceed to form $[(R^1N(CR^3)=NR^2)(R^4N(CR^6)=NR^5)(SiH_2Si_nH_{2n}SiH_2)]$; and h) separating the product $[(R^1N(CR^3)=NR^2)(R^4N(CR^6)=NR^5)(SiH_2Si_nH_{2n}SiH_2)]$ from the reaction mixture, wherein the reaction temperature may vary during the synthesis and is maintained such that the temperature of the reaction mixture is not allowed to drop below about 0° C. and not exceed about 300° C.

* * * * *

UNITED STATES PATENT AND TRADEMARK OFFICE
CERTIFICATE OF CORRECTION

Page 1 of 1

PATENT NO. : 9,453,035 B2
APPLICATION NO. : 15/088495
DATED : September 27, 2016
INVENTOR(S) : Antonio Sanchez et al.

It is certified that error appears in the above-identified patent and that said Letters Patent is hereby corrected as shown below:

On the Title Page

Item (72), add --Manish Khandelwal, Branchburg NJ (US)--.

Signed and Sealed this
Twelfth Day of December, 2017

Joseph Matal
*Performing the Functions and Duties of the
Under Secretary of Commerce for Intellectual Property and
Director of the United States Patent and Trademark Office*